US011813041B2

(12) United States Patent
Field et al.

(10) Patent No.: US 11,813,041 B2
(45) Date of Patent: Nov. 14, 2023

(54) PHOTODETECTOR ARCHITECTURES FOR TIME-CORRELATED SINGLE PHOTON COUNTING

(71) Applicant: HI LLC, Los Angeles, CA (US)

(72) Inventors: Ryan Field, Culver City, CA (US); Bruno Do Valle, Brighton, MA (US); Jacob Dahle, Arlington, MA (US); Rong Jin, Acton, MA (US); Sebastian Sorgenfrei, Playa Vista, CA (US)

(73) Assignee: HI LLC, Los Angeles, CA (US)

( * ) Notice: Subject to any disclaimer, the term of this patent is extended or adjusted under 35 U.S.C. 154(b) by 851 days.

(21) Appl. No.: 16/844,860

(22) Filed: Apr. 9, 2020

(65) Prior Publication Data

US 2020/0352445 A1 Nov. 12, 2020

Related U.S. Application Data

(60) Provisional application No. 62/880,025, filed on Jul. 29, 2019, provisional application No. 62/844,107, filed on May 6, 2019.

(51) Int. Cl.

*A61B 5/00* (2006.01)
*G01J 1/44* (2006.01)
*G04F 10/00* (2006.01)

(52) U.S. Cl.

CPC .......... *A61B 5/0082* (2013.01); *A61B 5/6803* (2013.01); *A61B 5/742* (2013.01);

(Continued)

(58) Field of Classification Search

CPC ..... A61B 5/0082; A61B 5/6803; A61B 5/742; G01J 1/44; G01J 2001/442; G01J 2001/4466; G04F 10/005

See application file for complete search history.

(56) References Cited

U.S. PATENT DOCUMENTS 4,018,534 A 4/1977 Thorn et al.
4,207,892 A 6/1980 Binder (Continued)

FOREIGN PATENT DOCUMENTS

CN 200950235 9/2007
CN 107865635 4/2018

(Continued)

OTHER PUBLICATIONS

Mehta, K., "Spread spectrum time-resolved diffuse optical measurement system for enhanced sensitivity in detecting human brain activity," Journal of Biomedical Optics. vol. 22(4), 2017. p. 1-8 (Year: 2017).*

(Continued)

*Primary Examiner* — Christopher Koharski
*Assistant Examiner* — Sean A Frith
(74) *Attorney, Agent, or Firm* — ALG Intellectual Property, LLC

(57) ABSTRACT

An exemplary photodetector system includes a plurality of photodetectors connected in parallel and a processor communicatively coupled to the plurality of photodetectors. The processor is configured to receive an accumulated output from the plurality of photodetectors. The accumulated output represents an accumulation of respective outputs from each of the plurality of photodetectors detecting photons during a predetermined measurement time period that occurs in response to a light pulse being directed toward a target within a body. The processor is further configured to determine, based on the accumulated output, a temporal distribution of photons detected by the plurality of photodetectors, and generate, based on the temporal distribution of photons, a histogram representing a light pulse response of the target within the body.

49 Claims, 17 Drawing Sheets

(52) U.S. Cl.
CPC .......... *G01J 1/44* (2013.01); *G01J 2001/442* (2013.01); *G01J 2001/4466* (2013.01); *G04F 10/005* (2013.01)

(56) References Cited

U.S. PATENT DOCUMENTS

| | | | |
|---|---|---|---|
| 4,281,645 | A | 8/1981 | Jobsis |
| 4,321,930 | A | 3/1982 | Jobsis |
| 4,515,165 | A | 5/1985 | Carroll |
| 4,655,225 | A | 4/1987 | Dahne et al. |
| 4,928,248 | A | 5/1990 | Takahashi et al. |
| 4,963,727 | A | 10/1990 | Cova |
| 4,995,044 | A | 2/1991 | Blazo |
| 5,088,493 | A | 2/1992 | Giannini |
| 5,090,415 | A | 2/1992 | Yamashita |
| 5,309,458 | A | 5/1994 | Carl |
| 5,386,827 | A | 2/1995 | Chance et al. |
| 5,528,365 | A | 6/1996 | Gonatas et al. |
| 5,625,458 | A | 4/1997 | Alfano et al. |
| 5,761,230 | A | 6/1998 | Oono et al. |
| 5,853,370 | A | 12/1998 | Chance et al. |
| 5,895,984 | A | 4/1999 | Renz |
| 5,929,982 | A | 7/1999 | Anderson |
| 5,983,120 | A | 11/1999 | Groner et al. |
| 5,987,045 | A | 11/1999 | Albares et al. |
| 6,163,715 | A | 12/2000 | Larsen et al. |
| 6,240,309 | B1 | 5/2001 | Yamashita et al. |
| 6,384,663 | B2 | 5/2002 | Cova et al. |
| 6,541,752 | B2 | 4/2003 | Zappa et al. |
| 6,640,133 | B2 | 10/2003 | Yamashita |
| 6,683,294 | B1 | 1/2004 | Herbert et al. |
| 6,748,254 | B2 | 6/2004 | O'Neil |
| 6,992,772 | B2 | 1/2006 | Block |
| 7,095,491 | B2 | 8/2006 | Forstner et al. |
| 7,356,365 | B2 | 4/2008 | Schurman |
| 7,507,596 | B2 | 3/2009 | Yaung et al. |
| 7,547,872 | B2 | 6/2009 | Niclass et al. |
| 7,613,504 | B2 | 11/2009 | Rowe |
| 7,705,284 | B2 | 4/2010 | Inoue et al. |
| 7,774,047 | B2 | 8/2010 | Yamashita et al. |
| 7,899,506 | B2 | 3/2011 | Xu et al. |
| 8,026,471 | B2 | 9/2011 | Itzler |
| 8,078,250 | B2 | 12/2011 | Chen et al. |
| 8,082,015 | B2 | 12/2011 | Yodh et al. |
| 8,115,170 | B2 | 2/2012 | Stellari et al. |
| 8,168,934 | B2 | 5/2012 | Niclass et al. |
| 8,352,012 | B2 | 1/2013 | Besio |
| 8,633,431 | B2 | 1/2014 | Kim |
| 8,754,378 | B2 | 6/2014 | Prescher et al. |
| 8,817,257 | B2 | 8/2014 | Herve |
| 8,937,509 | B2 | 1/2015 | Xu et al. |
| 8,986,207 | B2 | 3/2015 | Li |
| 9,012,860 | B2 | 4/2015 | Nyman et al. |
| 9,041,136 | B2 | 5/2015 | Chia |
| 9,058,081 | B2 | 6/2015 | Baxter |
| 9,076,707 | B2 | 7/2015 | Harmon |
| 9,101,279 | B2 | 8/2015 | Ritchey et al. |
| 9,131,861 | B2 | 9/2015 | Ince et al. |
| 9,157,858 | B2 | 10/2015 | Claps |
| 9,160,949 | B2 | 10/2015 | Zhang et al. |
| 9,176,241 | B2 | 11/2015 | Frach |
| 9,178,100 | B2 | 11/2015 | Webster et al. |
| 9,190,552 | B2 | 11/2015 | Brunel et al. |
| 9,201,138 | B2 | 12/2015 | Eisele et al. |
| 9,209,320 | B1 | 12/2015 | Webster |
| 9,257,523 | B2 | 2/2016 | Schneider et al. |
| 9,257,589 | B2 | 2/2016 | Niclass et al. |
| 9,299,732 | B2 | 3/2016 | Webster et al. |
| 9,299,873 | B2 | 3/2016 | Mazzillo et al. |
| 9,312,401 | B2 | 4/2016 | Webster |
| 9,316,735 | B2 | 4/2016 | Baxter |
| 9,331,116 | B2 | 5/2016 | Webster |
| 9,368,487 | B1 | 6/2016 | Su et al. |
| 9,401,448 | B2 | 7/2016 | Bienfang et al. |
| 9,407,796 | B2 | 8/2016 | Dinten et al. |
| 9,419,635 | B2 | 8/2016 | Kumar et al. |
| 9,431,439 | B2 | 8/2016 | Soga et al. |
| 9,442,201 | B2 | 9/2016 | Schmand et al. |
| 9,449,377 | B2 | 9/2016 | Sarkar et al. |
| 9,450,007 | B1 | 9/2016 | Motta et al. |
| 9,466,631 | B2 | 10/2016 | Fallica et al. |
| 9,476,979 | B2 | 10/2016 | Drader et al. |
| 9,529,079 | B1 | 12/2016 | Droz et al. |
| 9,535,157 | B2 | 1/2017 | Caley et al. |
| 9,574,936 | B2 | 2/2017 | Heinonen |
| 9,625,580 | B2 | 4/2017 | Kotelnikov et al. |
| 9,627,569 | B2 | 4/2017 | Harmon |
| 9,639,063 | B2 | 5/2017 | Dutton et al. |
| 9,640,704 | B2 | 5/2017 | Frey et al. |
| 9,658,158 | B2 | 5/2017 | Renna et al. |
| 9,659,980 | B2 | 5/2017 | McGarvey et al. |
| 9,671,284 | B1 | 6/2017 | Dandin |
| 9,681,844 | B2 | 6/2017 | Xu et al. |
| 9,685,576 | B2 | 6/2017 | Webster |
| 9,702,758 | B2 | 7/2017 | Nouri |
| 9,728,659 | B2 | 8/2017 | Hirigoyen et al. |
| 9,741,879 | B2 | 8/2017 | Frey et al. |
| 9,753,351 | B2 | 9/2017 | Eldada |
| 9,767,246 | B2 | 9/2017 | Dolinsky et al. |
| 9,768,211 | B2 | 9/2017 | Harmon |
| 9,773,930 | B2 | 9/2017 | Motta et al. |
| 9,804,092 | B2 | 10/2017 | Zeng et al. |
| 9,812,438 | B2 | 11/2017 | Schneider et al. |
| 9,831,283 | B2 | 11/2017 | Shepard et al. |
| 9,851,302 | B2 | 12/2017 | Mattioli Della Rocca et al. |
| 9,869,753 | B2 | 1/2018 | Eldada |
| 9,881,963 | B1 | 1/2018 | Chen et al. |
| 9,882,003 | B1 | 1/2018 | Aharoni |
| 9,886,095 | B2 | 2/2018 | Pothier |
| 9,899,544 | B1 | 2/2018 | Mazzillo et al. |
| 9,899,557 | B2 | 2/2018 | Muscara' et al. |
| 9,939,316 | B2 | 4/2018 | Scott et al. |
| 9,939,536 | B2 | 4/2018 | O'Neill et al. |
| 9,946,344 | B2 | 4/2018 | Ayaz et al. |
| D817,553 | S | 5/2018 | Aaskov et al. |
| 9,983,670 | B2 | 5/2018 | Coleman |
| D825,112 | S | 8/2018 | Saez |
| 10,103,513 | B1 | 10/2018 | Zhang et al. |
| 10,158,038 | B1 | 12/2018 | Do Valle et al. |
| 10,340,408 | B1 | 7/2019 | Katnani |
| 10,424,683 | B1 | 9/2019 | Do Valle |
| 10,483,125 | B2 | 11/2019 | Inoue |
| 10,515,993 | B2 | 12/2019 | Field et al. |
| 10,533,893 | B2 | 1/2020 | Leonardo |
| 10,558,171 | B2 | 2/2020 | Kondo |
| 10,594,306 | B2 | 3/2020 | Dandin |
| 10,627,460 | B2 | 4/2020 | Alford et al. |
| 10,697,829 | B2 | 6/2020 | Delic |
| 10,772,561 | B2 | 9/2020 | Donaldson |
| 10,825,847 | B2 | 11/2020 | Furukawa |
| 10,912,504 | B2 | 2/2021 | Nakaji |
| 10,976,386 | B2 | 4/2021 | Alford |
| 10,983,177 | B2 | 4/2021 | Jiménez-Martínez |
| 10,996,293 | B2 | 5/2021 | Mohseni |
| 11,006,876 | B2 | 5/2021 | Johnson |
| 11,006,878 | B2 | 5/2021 | Johnson |
| 2004/0057478 | A1 | 3/2004 | Saito |
| 2004/0078216 | A1 | 4/2004 | Toto |
| 2004/0160996 | A1 | 8/2004 | Giorgi et al. |
| 2006/0197452 | A1 | 9/2006 | Zhang |
| 2007/0038116 | A1 | 2/2007 | Yamanaka |
| 2007/0083097 | A1 | 4/2007 | Fujiwara |
| 2008/0021341 | A1 | 1/2008 | Harris et al. |
| 2009/0012402 | A1 | 1/2009 | Mintz |
| 2009/0163775 | A1 | 6/2009 | Barrett |
| 2009/0313048 | A1 | 12/2009 | Kahn et al. |
| 2010/0210952 | A1 | 8/2010 | Taira et al. |
| 2011/0208675 | A1 | 8/2011 | Shoureshi et al. |
| 2012/0029304 | A1 | 2/2012 | Medina et al. |
| 2012/0101838 | A1 | 4/2012 | Lingard et al. |
| 2013/0030267 | A1 | 1/2013 | Lisogurski |
| 2013/0144644 | A1 | 6/2013 | Simpson |
| 2013/0342835 | A1 | 12/2013 | Blacksberg |

(56) References Cited

U.S. PATENT DOCUMENTS

2014/0027607 A1* 1/2014 Mordarski ................ G01J 1/44 250/206
2014/0066783 A1 3/2014 Kiani
2014/0185643 A1 7/2014 McComb et al.
2014/0211194 A1 7/2014 Pacala et al.
2014/0275891 A1 9/2014 Muehlemann et al.
2014/0289001 A1 9/2014 Shelton
2015/0041625 A1 2/2015 Dutton
2015/0057511 A1 2/2015 Basu
2015/0077279 A1 3/2015 Song
2015/0094552 A1 4/2015 Golda
2015/0150505 A1 6/2015 Kaskoun et al.
2015/0182136 A1 7/2015 Durduran et al.
2015/0192677 A1 7/2015 Yu et al.
2015/0293224 A1 10/2015 Eldada et al.
2015/0327777 A1 11/2015 Kostic et al.
2015/0355019 A1* 12/2015 Nouri ........................ G01J 1/44 250/208.2
2015/0364635 A1 12/2015 Bodlovic et al.
2016/0049765 A1 2/2016 Eldada
2016/0119983 A1 4/2016 Moore
2016/0150963 A1 6/2016 Roukes et al.
2016/0161600 A1 6/2016 Eldada et al.
2016/0181302 A1 6/2016 McGarvey et al.
2016/0198961 A1* 7/2016 Homyk ................ A61B 5/0066 600/476
2016/0218236 A1 7/2016 Dhulla et al.
2016/0247301 A1 8/2016 Fang
2016/0268331 A1* 9/2016 Parmesan ............. G01S 7/4865
2016/0278715 A1 9/2016 Yu et al.
2016/0287107 A1 10/2016 Szabados
2016/0341656 A1 11/2016 Liu et al.
2016/0345880 A1 12/2016 Nakaji et al.
2016/0357260 A1 12/2016 Raynor et al.
2017/0030769 A1 2/2017 Clemens et al.
2017/0047372 A1 2/2017 McGarvey et al.
2017/0052065 A1 2/2017 Sharma et al.
2017/0118423 A1 4/2017 Zhou et al.
2017/0124713 A1 5/2017 Jurgenson et al.
2017/0131143 A1 5/2017 Andreou et al.
2017/0139041 A1 5/2017 Drader et al.
2017/0141100 A1 5/2017 Tseng et al.
2017/0176579 A1 6/2017 Niclass et al.
2017/0176596 A1 6/2017 Shpunt et al.
2017/0179173 A1 6/2017 Mandai et al.
2017/0186798 A1 6/2017 Yang et al.
2017/0202518 A1 7/2017 Furman et al.
2017/0215811 A1* 8/2017 Newberry .......... A61B 5/14532
2017/0265822 A1 9/2017 Du
2017/0276545 A1 9/2017 Henriksson
2017/0281086 A1 10/2017 Donaldson
2017/0299700 A1 10/2017 Pacala et al.
2017/0303789 A1 10/2017 Tichauer et al.
2017/0314989 A1 11/2017 Mazzillo et al.
2017/0363467 A1 12/2017 Clemens et al.
2018/0003821 A1 1/2018 Imai
2018/0014741 A1 1/2018 Chou
2018/0020960 A1 1/2018 Sarussi
2018/0027196 A1 1/2018 Yang et al.
2018/0039053 A1 2/2018 Kremer et al.
2018/0045816 A1 2/2018 Jarosinski et al.
2018/0062345 A1 3/2018 Bills et al.
2018/0069043 A1 3/2018 Pan et al.
2018/0070830 A1* 3/2018 Sutin ........................ A61B 5/72
2018/0070831 A1 3/2018 Sutin et al.
2018/0078151 A1* 3/2018 Allec .................. A61B 5/6801
2018/0081061 A1 3/2018 Mandai et al.
2018/0089531 A1 3/2018 Geva et al.
2018/0089848 A1 3/2018 Yang et al.
2018/0090526 A1 3/2018 Mandai et al.
2018/0090536 A1* 3/2018 Mandai ............. H01L 27/14643
2018/0103528 A1 4/2018 Moore
2018/0103861 A1 4/2018 Sutin et al.
2018/0156660 A1 6/2018 Turgeon
2018/0185667 A1 7/2018 Huang
2018/0195900 A1* 7/2018 Delic ................... H01L 31/107
2018/0296094 A1 10/2018 Nakamura
2018/0366342 A1 12/2018 Inoue et al.
2019/0026849 A1 1/2019 Demeyer
2019/0088697 A1 3/2019 Furukawa et al.
2019/0090526 A1 3/2019 Alshatwi et al.
2019/0091483 A1 3/2019 Deckert
2019/0113385 A1 4/2019 Fukuchi
2019/0167211 A1 6/2019 Everman et al.
2019/0175068 A1 6/2019 Everdell
2019/0200888 A1 7/2019 Poltorak
2019/0261869 A1 8/2019 Franceschini
2019/0298158 A1 10/2019 Dhaliwal
2019/0343395 A1 11/2019 Cussac
2019/0355773 A1 11/2019 Field et al.
2019/0355861 A1 11/2019 Katnani
2019/0363210 A1 11/2019 Do Valle
2019/0378869 A1 12/2019 Field et al.
2019/0388018 A1 12/2019 Horstmeyer
2019/0391213 A1 12/2019 Alford
2020/0056263 A1 2/2020 Bhattacharyya
2020/0057115 A1 2/2020 Jiménez-Martínez
2020/0057116 A1 2/2020 Zorzos et al.
2020/0088811 A1 3/2020 Mohseni
2020/0109481 A1 4/2020 Sobek
2020/0123416 A1 4/2020 Bhattacharyya
2020/0182692 A1 6/2020 Lilic
2020/0191883 A1 6/2020 Bhattacharyya
2020/0196932 A1 6/2020 Johnson
2020/0241094 A1 7/2020 Alford
2020/0256929 A1 8/2020 Ledbetter et al.
2020/0309873 A1 10/2020 Ledbetter et al.
2020/0315510 A1 10/2020 Johnson
2020/0334559 A1 10/2020 Anderson
2020/0337624 A1 10/2020 Johnson
2020/0341081 A1 10/2020 Mohseni et al.
2020/0348368 A1 11/2020 Garber et al.
2020/0381128 A1 12/2020 Pratt
2020/0390358 A1 12/2020 Johnson
2020/0393902 A1 12/2020 Mann et al.
2020/0400763 A1 12/2020 Pratt
2021/0013974 A1 1/2021 Deng et al.
2021/0015385 A1 1/2021 Katnani
2021/0011094 A1 2/2021 Bednarke
2021/0041512 A1 2/2021 Pratt
2021/0063510 A1 3/2021 Ledbetter
2021/0139742 A1 5/2021 Seidman

FOREIGN PATENT DOCUMENTS

EP 0656536 4/2004
EP 2294973 3/2011
EP 3419168 12/2018
EP 3487072 5/2019
WO 8804034 6/1988
WO 1999053577 10/1999
WO 2008144831 12/2008
WO 2012135068 10/2012
WO 2013034770 3/2013
WO 2013066959 5/2013
WO 2015052523 4/2015
WO 2015109005 7/2015
WO 2016166002 10/2016
WO 2017004663 1/2017
WO 2017130682 8/2017
WO 2017150146 9/2017
WO 2017203936 11/2017
WO 2018007829 1/2018
WO 2018033751 2/2018
WO 2018122560 7/2018

OTHER PUBLICATIONS

Partial Search Report received in International Application No. PCT/US2020/027537, dated Jul. 17, 2020.

Mita, et al., "High-Speed and Compact Quenching Circuit for Single-Photon Avalanche Diodes," IEEE Transactions on Instru-

(56) References Cited

OTHER PUBLICATIONS mentation and Measurement, vol. 57, No. 3, Mar. 2008. pp. 543-547.
International Search Report and Written Opinion received in International Application No. PCT/US20/028820, dated Aug. 26, 2020.
International Search Report and Written Opinion received in International Application No. PCT/US20/027537, dated Sep. 7, 2020.
International Search Report and Written Opinion received in International Application No. PCT/US20/034062, dated Aug. 26, 2020.
"emojipedia.org", https://emojipedia.org (accessed May 27, 2021).
"International Search Report and Written Opinion received in International Application No. PCT/2021/018188".
"International Search Report and Written Opinion received in International Application No. PCT/US2021/018155".
"International Search Report and Written Opinion received in International Application No. PCT/US2021/018187".
"International Search Report and Written Opinion received in International Application No. PCT/US2021/018190".
"scienceofpeople.com/emojis", https://www.scienceofpeople.com/emojis/ (accessed May 27, 2021).
Hebert, et al.,"Spatiotemporal image correlation spectroscopy (STICS) theory, verification, and application to protein velocity mapping in living CHO cells", Biophysical journal 88, No. 5 (2005): 3601-3614.
Kheng, et al.,"Image Processing", https://www.comp.nus.edu.sg/~cs4243/lecture/imageproc.pdf, Mar. 9, 2014.
Sneha, et al.,"Understanding Correlation", https://www.allaboutcircuits.com/technical-articles/understanding-correlation/, Jan. 4, 2017.
Xu, et al.,"A 655 μW Silicon Photomultiplier-Based NIRS/EEG/EIT Monitoring ASIC for Wearable Functional Brain Imaging", IEEE Transactions on Biomedical Circuits and Systems, IEEE, US, vol. 12, No. 6, Dec. 1, 2018.
Zucconi, et al.,"The Autocorrelation Function", https://www.alanzucconi.com/2016/06/06/autocorrelation-function/, Jun. 6, 2016.
Dutton, et al., A Time-Correlated Single-Photon-Counting Sensor with 14GS/s Histogramming Time-to-Digital, 2015 IEEE International Solid-State Circuits Conference ISSCC 2015 / Session 11 / Sensors and Imagers for Life Sciences / 11.5.
Gnecchi, et al., A 1×16 SiPM Array for Automotive 3D Imaging LiDAR Systems.
Mandai, et al., A 4×4×416 digital SiPM array with 192 TDCs for multiple high-resolution timestamp acquisition, 2013 JINST 8 PO5024.
Parmesan, et al., A 256×256 SPAD array with in-pixel Time to Amplitude Conversion for Fluorescence Lifetime Imaging Microscopy, 2015.
Zhang, et al., A CMOS SPAD Imager with Collision Detection and 128 Dynamically Reallocating TDCs for Single-Photon Counting and 3D Time-of-Flight Imaging, Sensors (Basel, Switzerland), 18(11), 4016.
International Search Report and Written Opinion received in International Application No. PCT/US2019/019317 dated May 28, 2019.
Partial Search Report received in International Application No. PCT/2020/028820.
Blutman, et al., "A 0.1 pJ Freeze Vernier Time-to-Digital Converter in 65nm CMOS," 2014 international Symposium on Circuits and Systems (ISCAS), Melbourne, Australia.
Dalla Mora, et al., "Memory effect in silicon time-gated single-photon avalanche diodes," Journal of Applied Physics 117, 114501 (2015).
De Heyn, et al., "A fast start-up 3GHz-10GHz digitally controlled oscillator for UWB impulse radio in 90nm CMOS," 2007 European Solid-State Circuits Conference—(ESSCIRC), Munich, Germany, pp. 484-487.
Fisher, et al., "A Reconfigurable Single-Photon-Counting Integrating Receiver for Optical Communications," IEEE Journal of Solid-State Circuits, vol. 48, No. 7, Jul. 2013, https://www.researchgate.net/publication/260626902.
Gallivanoni, et al., "Progress in Quenching Circuits for Single Photon Avalanche Diodes," IEEE Transactions on Nuclear Science, vol. 57, No, 6, Dec. 2010.
Henderson, et al., "5.7 A 256×256 40nrn/90nm CMOS 3D-Stacked 120dB Dynamic-Range Reconfigurable Time-Resolved SPAD Imager," 2019 IEEE International Solid-State Circuits Conference—(ISSCC), San Francisco, CA, USA, 2019, pp. 106-108. doi: 10.1109/ISSCC.2019.8662355.
Henderson, et al., "A 192×128 Time Correlated SPAD Image Sensor in 40-nm CMOS Technology," IEEE Journal of Solid-State Circuits, IEEE Journal of Solid-State Circuits, 2019.
Richardson, et al., "A 32×32 50ps resolution 10 bit time to digital converter array in 130nm CMOS for time correlated imaging," CICC 2009 Proceedings of the IEEE 2009 Custom Integrated Circuits Cenference. IEEE Society, San Jose, U.S.A., pp. 77-80, CiCC 2009, San Jose, U.S.A., Sep. 13, 2009. https://doi.org/doi:10.1109/CICC.2009.5280890.
International Search Report and Written Opinion received in International Application No. PCT/US2018/058580 dated Feb. 12, 2019.
International Search Report and Written Opinion received in International Application No. PCT/US2018/062777 dated Feb. 13, 2019.
Non-Final Office Action received in U.S. Appl. No. 16/177,351 dated Apr. 1, 2019.
Non-Final Office Action received in U.S. Appl. No. 16/370,991 dated Feb. 10, 2020.
Non-Final Office Action received in U.S. Appl. No. 16/537,360 dated Feb. 25, 2020.
Bellis, Stephen et al., "Photon counting imaging: the Digital APD," Society of Photo-Optical Instrumentation Engineers (SPIE) Conference Series, Feb. 2006, vol. 6068, pp. 111-120.
Cambie, Dario et al., "Every photon counts: understanding and optimizing photon paths in luminescent solar concentrator-based photomicroreactors (LSC-PMs)," React. Chem. Eng., 2017, 2, 561-566.
Harmon, Eric S. et al., "Compound Semiconductor SPAD Arrays," LightSpin Technologies, http://www.lightspintech.com/publications.html.
Lee, et al., "High-Performance Back-Illuminated Three-Dimensional Stacked Single-Photon Avalanche Diode Implemented in 45-nm CMOS Technology," IEEE journal of Selected Topics in Quantum Electronics 6, 1-9 (2018).
Mora, Alberto D. et al., "Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.

* cited by examiner

PHOTODETECTOR ARCHITECTURES FOR TIME-CORRELATED SINGLE PHOTON COUNTING

RELATED APPLICATIONS

The present application claims priority under 35 U.S.C. § 119(e) to U.S. Provisional Patent Application No. 62/880,025, filed Jul. 29, 2019, and to U.S. Provisional Patent Application No. 62/844,107, filed May 6, 2019. These applications are incorporated herein by reference in their respective entireties.

BACKGROUND INFORMATION

Detecting neural activity in the brain is useful for medical diagnostics, imaging, neuroengineering, brain-computer interfacing, and a variety of other diagnostic and consumer-related applications. For example, it may be desirable to detect neural activity in the brain of a patient to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. One technique to measure such responses is time-correlated single-photon counting (TCSPC). Time-correlated single-photon counting detects single photons and measures a time of arrival of the photons with respect to a reference signal (e.g., a light source). By repeating the light pulses, TCSPC may accumulate a sufficient number of photon events to determine statistically a histogram representing the distribution of photons detected. Based on the histogram of photon distribution, the response of tissue to light pulses may be determined to determine neural activity and other attributes of the brain.

A photodetector capable of detecting a single photon is an example of a non-invasive detector that can be used to detect neural activity within the brain. Photodetectors may be used to detect single photons to perform TCSPC. However, repeatedly detecting single photons may be difficult, as conventional photodetectors often have a dead time that may slow down a detection rate. Further, using multiple photodetectors may increase resources needed to operate such systems.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Photodetector systems for time-correlated single-photon counting (TCSPC) are described herein. The photodetector systems described herein each include a plurality of photodetectors connected in parallel and a processor communicatively coupled to the plurality of photodetectors. The processor is configured to receive an accumulated output from the plurality of photodetectors. The accumulated output represents an accumulation of respective outputs from each of the plurality of photodetectors detecting photons during a predetermined measurement time period that occurs in response to a light pulse being directed toward a target within a body. The processor is further configured to determine, based on the accumulated output, a temporal distribution of photons detected by the plurality of photodetectors, and generate, based on the temporal distribution of photons, a histogram representing a light pulse response of the target within the body.

The photodetector systems described herein may be used to perform TCSPC by accumulating the respective outputs from the plurality of photodetectors while abstaining from resetting the photodetectors during the predetermined measurement time period. For example, once a photodetector detects a photon, the output of the photodetector may be held (e.g., not reset) during the predetermined measurement time period. By holding the outputs of the photodetectors, the respective outputs may be accumulated and detected photons may be counted using a minimal number of analog-to-digital converters (ADCs) or time-to-digital converters (TDCs) per photodetector. Additionally, in some implementations, ADCs with a relatively slow sampling rate may be used to sample the accumulated signals to count the photons. Such architectures may allow photodetector systems to perform TCSPC while conserving resources, such as power consumption, system area, etc., and/or with greater efficiency in photon detection compared to conventional photodetector systems. These and other benefits and/or advantages that may be provided by the systems and methods described herein will be made apparent by the following detailed description.

Figure 1:
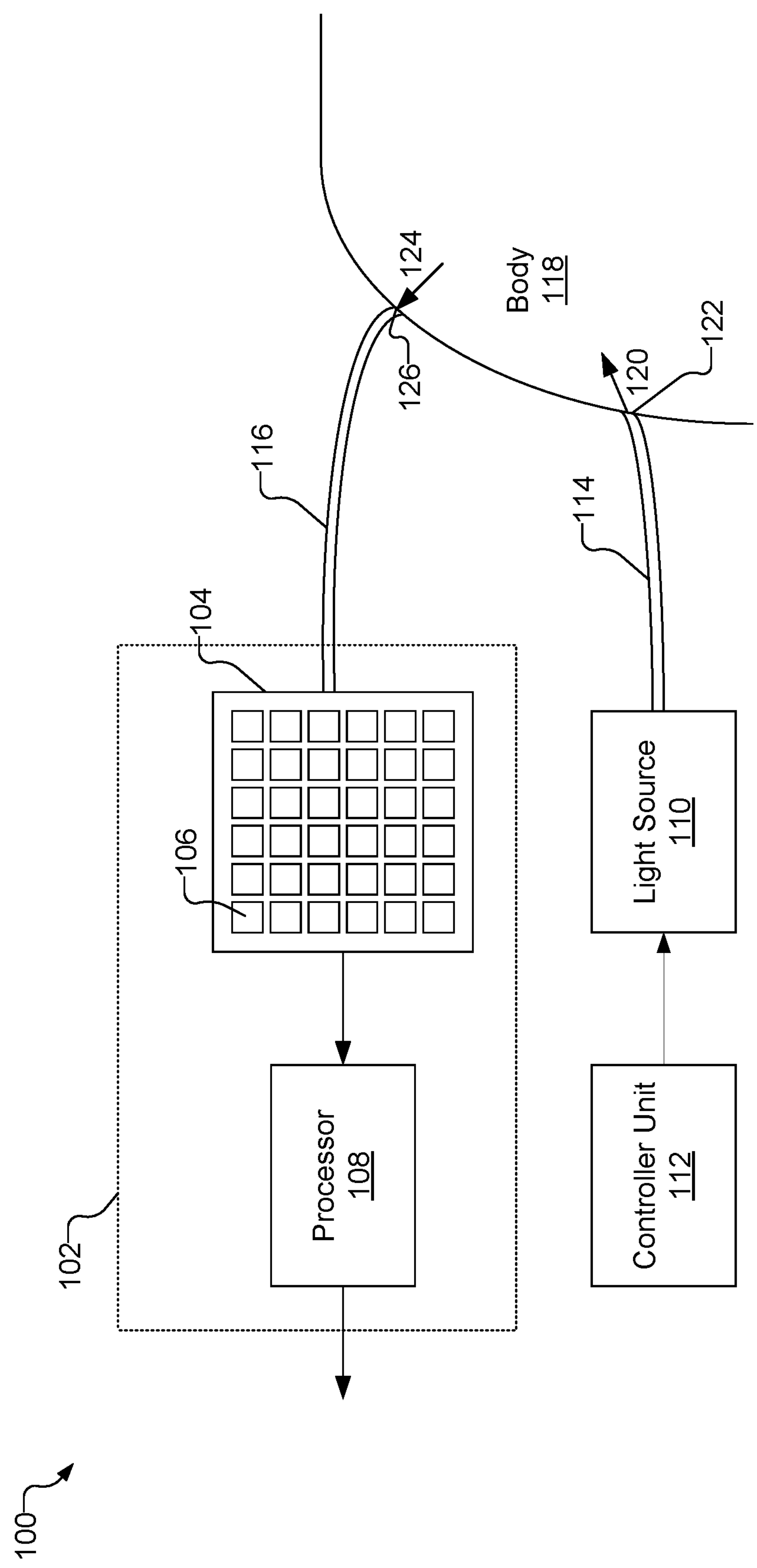
FIG. 1 illustrates an exemplary configuration of a photodetector system for TCSPC according to principles described herein.

FIG. 1 shows an exemplary configuration 100 in which a photodetector system 102 is configured to perform TCSPC. As shown, photodetector system 102 includes a photodetector array 104 composed of a plurality of individual photodetectors (e.g., photodetector 106) and a processor 108 coupled to photodetector array 104. Other components included in configuration 100 (e.g., a light source 110, a controller unit 112, and optical fibers 114 and 116) are not shown to be included in photodetector system 102 in FIG. 1. However, one or more of these components may, in certain embodiments, be considered to be a part of photodetector system 102.

Photodetectors 106 may each be implemented by any suitable circuit configured to detect individual photons of light incident upon photodetectors 106. For example, each photodetector 106 may be implemented by a single photon avalanche diode (SPAD) circuit. Each photodetector 106 may include a control circuit, which may include a quench circuit, a reset circuit, and/or a fast-gating circuit.

Processor 108 may be implemented by one or more physical processing (e.g., computing) devices. In some examples, processor 108 may execute software configured to perform one or more of the operations described herein.

Light source 110 may be implemented by any suitable component configured to generate and emit high coherence light (e.g., light that has a coherence length of at least 5 centimeters) at a predetermined center wavelength. For example, light source 110 may be implemented by a high-coherence laser diode.

Light source 110 is controlled by controller unit 112, which may be implemented by any suitable computing device (e.g., processor 108), integrated circuit, and/or combination of hardware and/or software as may serve a particular implementation. In some examples, controller unit 112 is configured to control light source 110 by turning light source 110 on and off and/or setting an intensity of light generated by light source 110. Controller unit 112 may be manually operated by a user, or may be programmed to control light source 110 automatically.

Light emitted by light source 110 travels via an optical fiber 114 (e.g., a single-mode fiber or a multi-mode fiber) to a body 118 of a subject. In some implementations, body 118 is a head or any other body part of a human or other animal. Alternatively, body 118 may be a non-living object. For illustrative purposes, it will be assumed in the examples provided herein that body 118 is a human head.

As indicated by arrow 120, the light emitted by light source 110 enters body 118 at a first location 122 on body 118. To this end, a distal end of fiber 114 may be positioned at (e.g., right above or physically attached to) first location 122 (e.g., to a scalp of the subject). In some examples, the light may emerge from fiber 114 and spread out to a certain spot size on body 118 to fall under a predetermined safety limit.

As shown, a proximal end of optical fiber 116 (e.g., a multi-mode optical fiber) is positioned at (e.g., right above or physically attached to) output location 126. In this manner, optical fiber 116 may collect light as it exits body 124 at location 126 and carry the light to photodetector array 104. The light may pass through one or more lenses and/or other optical elements (not shown) that direct the light onto each of the photodetectors 106 included in photodetector array 104.

Photodetectors 106 may be connected in parallel in photodetector array 104. An output of each of photodetectors 106 may be accumulated to generate an accumulated output of photodetector array 104. Processor 108 may receive the accumulated output and determine, based on the accumulated output, a temporal distribution of photons detected by photodetectors 106. Processor 108 may then generate, based on the temporal distribution, a histogram representing a light pulse response of a target in body 118. Example embodiments of accumulated outputs are described herein.

Figure 2:
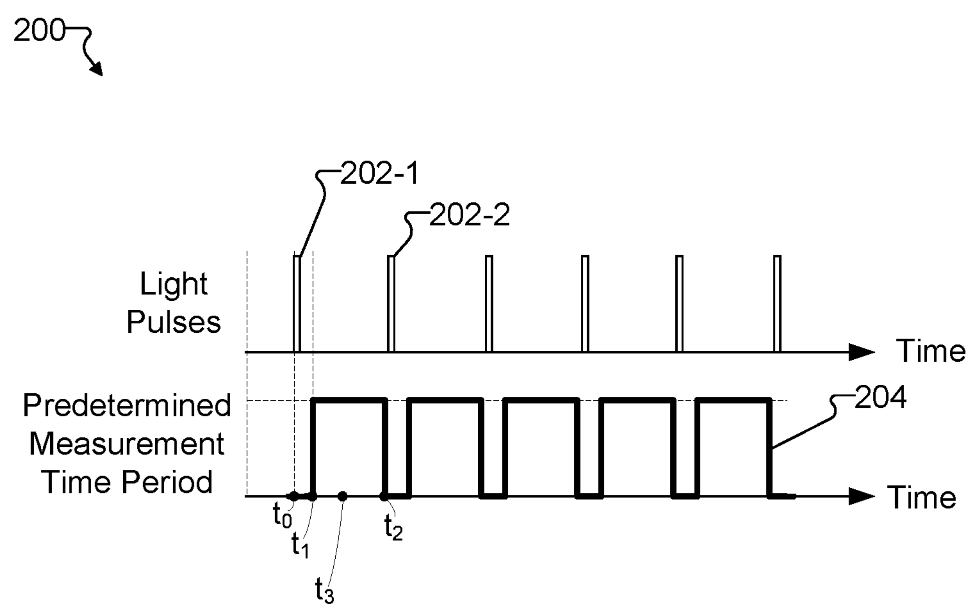
FIG. 2 illustrates an exemplary timing diagram for TCSPC using photodetector architectures according to principles described herein.

FIG. 2 illustrates an exemplary timing diagram 200 for performing TCSPC using photodetector systems, such as photodetector system 102. Photodetector system 102 may be configured to perform TCSPC by directing light pulses (e.g., laser pulses) toward a target within a body (e.g., body 118). The light pulses may be short (e.g., 10-2000 picoseconds (ps)) and repeated at a high frequency (e.g., between 100,000 hertz (Hz) and 100 megahertz (MHz)). The light pulses may reflect off of the target and be detected by photodetector system 102. Photodetector system 102 may measure a time relative to the light pulse for each detected photon. By counting the number of photons detected at each time relative to each light pulse repeated over a plurality of light pulses, photodetector system 102 may generate a histogram that represents a light pulse response of the target.

For example, timing diagram 200 shows a sequence of light pulses 202 (e.g., light pulses 202-1 and 202-2) that may be applied to the target (e.g., tissue within a brain of a user, a fluorescent material used as a probe in a body of a user, etc.). Timing diagram 200 also shows a pulse wave 204 representing predetermined measurement time periods during which the photodetectors are configured to detect photons. Referring to light pulse 202-1, light pulse 202-1 is applied at a time $t_0$. At a time $t_1$, a first instance of the predetermined measurement time period begins. The photodetectors may be armed at time $t_1$, enabling the photodetectors to detect photons reflecting off the target during the predetermined measurement time period. In this example, time $t_1$ is set to be at a certain time after time $t_0$, which may minimize photons detected directly from the laser pulse, before the laser pulse reaches the target. However, in some alternative examples, time $t_1$ is set to be equal to time $t_0$.

At a time $t_2$, the predetermined measurement time period ends. In some examples, the photodetectors may be disarmed at time $t_2$. In other examples, the photodetectors may be reset (e.g., disarmed and re-armed) at time $t_2$ or at a time subsequent to time $t_2$. During the predetermined measurement time period, the photodetectors may detect photons reflected off of the target. The photodetectors may be configured to remain armed during the predetermined measurement time period such that the photodetectors maintain an output upon detecting a photon during the predetermined measurement time period. For example, a photodetector may detect a photon at a time $t_3$, which is during the predetermined measurement time period between times $t_1$ and $t_2$. The photodetector may be configured to provide an output indicating that the photodetector has detected a photon. The photodetector may be configured to continue providing the output until time $t_2$, when the photodetector may be disarmed and/or reset. By holding the outputs of the photodetectors, photodetector system 102 may generate an accumulated output from the plurality of photodetectors. Photodetector system 102 may sample the accumulated output to determine times at which photons are detected by the plurality of photodetectors to generate the histogram.

Figure 3:
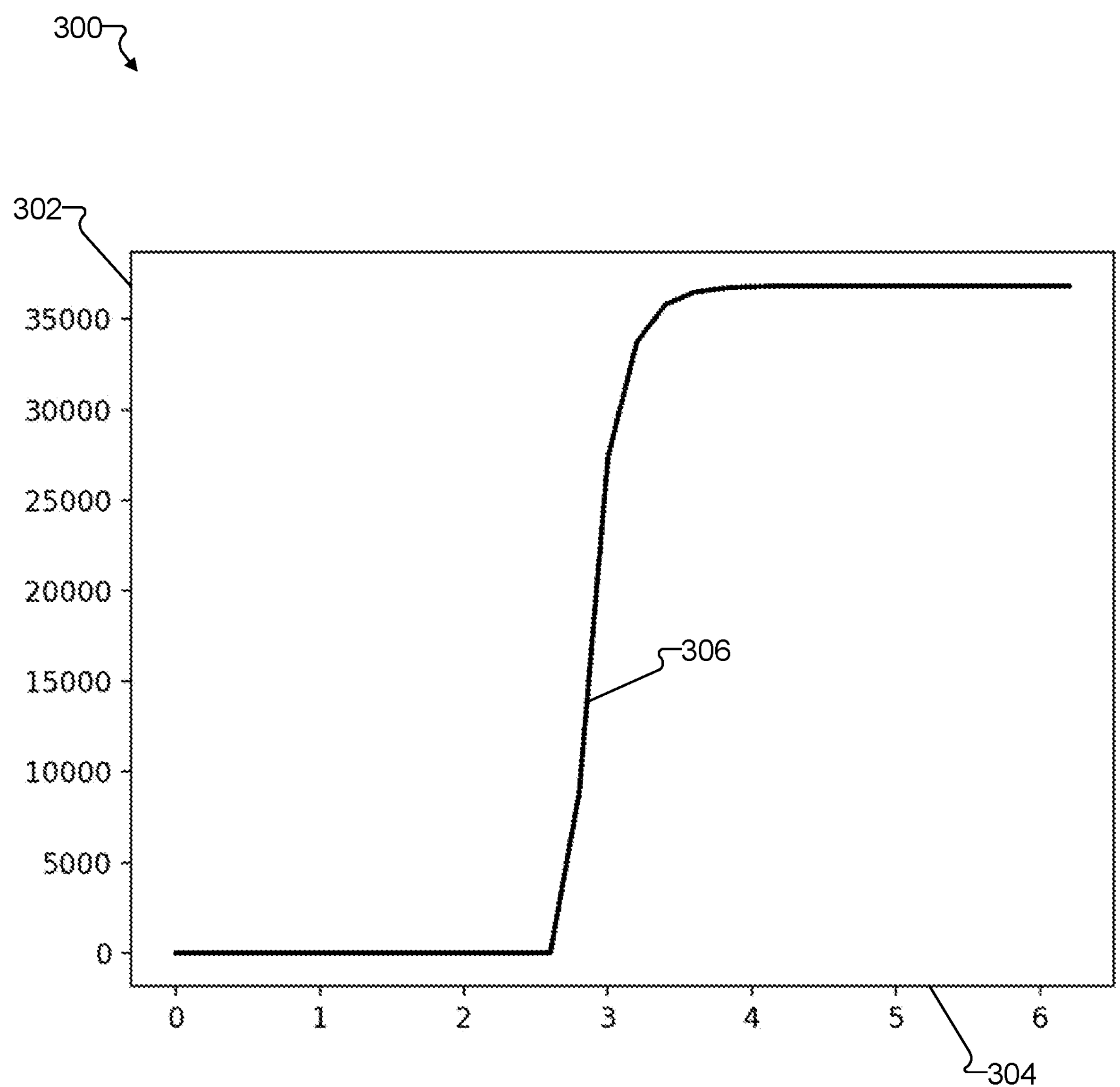
FIGS. 3-4 illustrate exemplary histograms for TCSPC using photodetector architectures according to principles described herein.

FIG. 3 illustrates an exemplary histogram 300 that may be generated by a photodetector system (e.g., photodetector system 102) performing TCSPC. Specifically, histogram 300 is a cumulative distribution function (CDF) showing a cumulative distribution of photons detected over a plurality of laser pulses (e.g., 50,000 to 2,000,000). Histogram 300 shows a number of photons on a y-axis 302 and time bins on an x-axis 304. A distribution curve 306 plots an accumulated number of photons detected by a corresponding time bin over the plurality of laser pulses. Time bins may correspond to nanoseconds, picoseconds, or any predetermined measurement time period normalized to any suitable desired step count numbering. In this example histogram 300, distribution curve 306 shows that an insignificant number of photons are detected from time 0 to approximately time 2.5. Distribution curve 306 further shows substantially all photons detected from the target are detected between approximately time 2.5 and time 4, with each point on distribution curve 306 showing a number of photons counted to that point in time over the plurality of light pulses.

Figure 4:
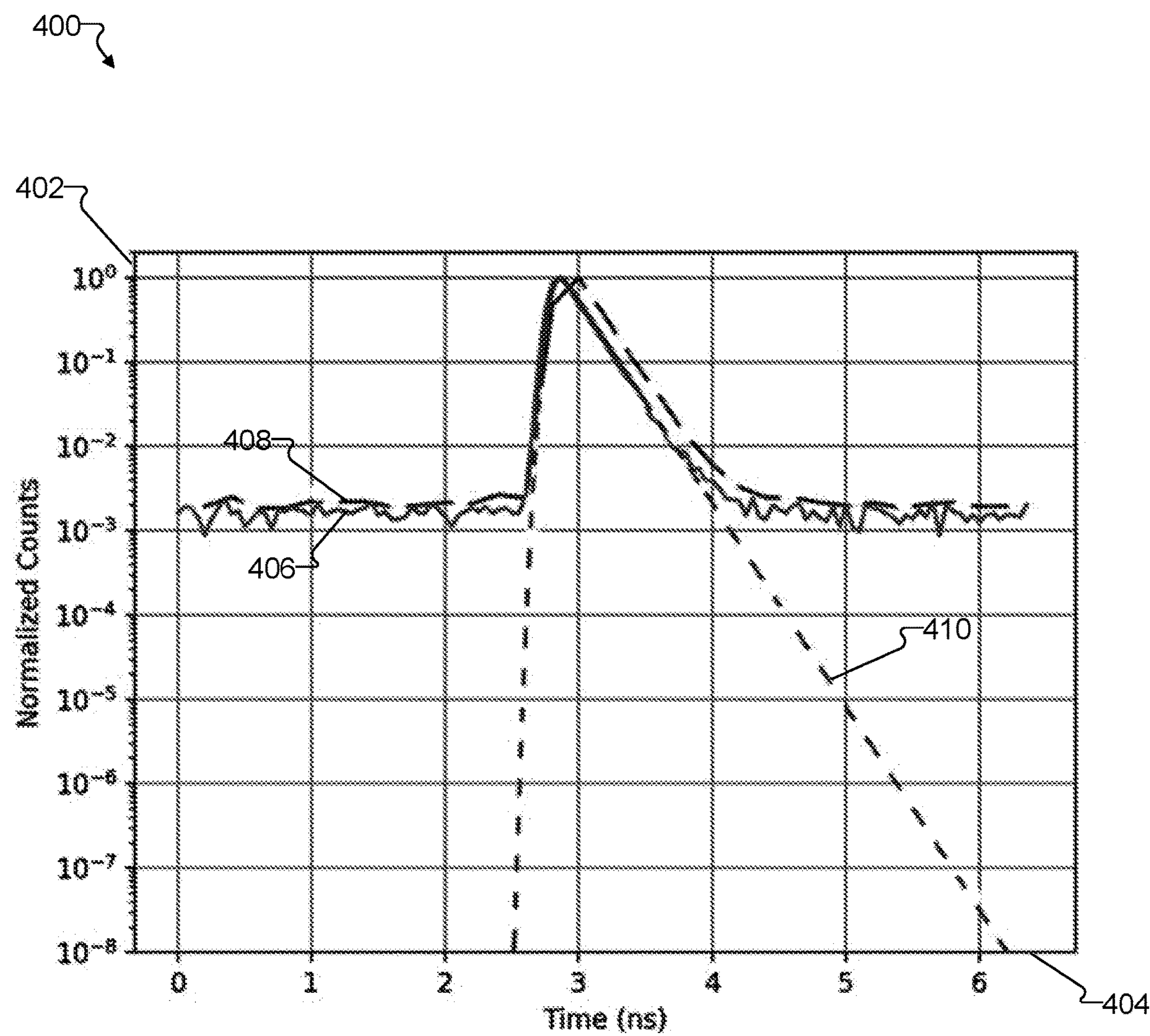

FIG. 4 illustrates another exemplary histogram 400 that may be generated by a photodetector system (e.g., photodetector system 102) performing TCSPC. Specifically, histogram 400 is a temporal point spread function (TPSF) representing a light pulse response of a target in a body (e.g., body 118). Histogram 400 shows a normalized count of photons on a y-axis 402 and time bins on an x-axis 404. Histogram 400 includes a first TPSF curve 406 (shown in a solid line on histogram 400), a second TPSF curve 408 (shown in a dashed line on histogram 400), and a third TPSF curve 410 (shown in a dotted line on histogram 400). In this example, first TPSF curve 406 shows a temporal point spread function determined from photon counts detected by photodetector system 102 over a plurality of laser pulses. For each time bin, first TPSF curve 406 shows a normalized number of photons detected in that time bin. Second TPSF curve 408 shows a temporal point spread function determined based on histogram 300, taking a derivative of the cumulative distribution function represented by distribution curve 306. As the number of photons detected in each time bin may be aggregated (i.e., integrated) to generate a cumulative distribution function, conversely, the temporal point spread function may be determined by deriving the CDF. Third TPSF curve 410 shows an ideal temporal point spread function. As shown, first TPSF curve 406 and second TPSF curve 408 both track substantially closely the ideal TSPF curve shown by third TPSF curve 410. The closeness of each of the TPSF curves may show an efficacy of both methods of determining TPSF curves using TCSPC by photodetector system 102.

Figure 5:
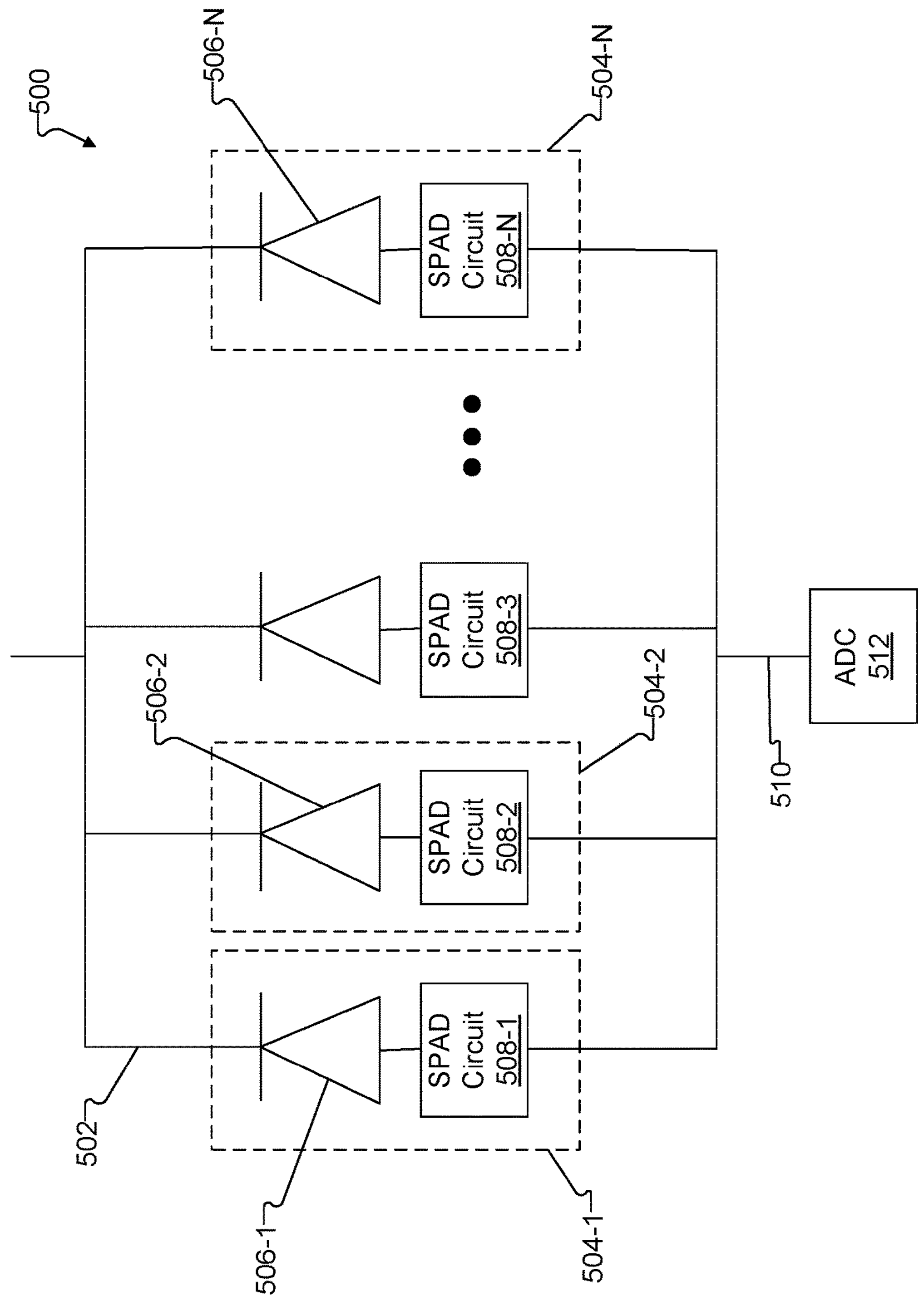
FIG. 5 illustrates an exemplary photodetector array of a photodetector system for TCSPC according to principles described herein.

FIG. 5 illustrates an exemplary configuration 500 of a photodetector array 502 (e.g., an implementation of photodetector array 104) that may be part of an exemplary analog implementation of a photodetector system for TCSPC. Photodetector array 502 includes a plurality of photodetectors 504 (photodetectors 504-1 through 504-N) connected in parallel. In configuration 500, photodetectors 504 each include a SPAD 506 and a SPAD circuit 508. For example, photodetector 504-1 includes a SPAD 506-1 and a SPAD circuit 508-1.

SPAD 506-1 may be implemented by any suitable single photon avalanche diode configured to detect single photons. SPAD circuit 508-1 may include a quench circuit, a reset circuit, and a fast-gating circuit, implemented in any suitable manner. Example SPADs and SPAD circuits include those described in U.S. Pat. No. 10,158,038, incorporated herein by reference in its entirety.

As described above, SPAD 506-1 is configured to detect photons that reflect off of a target in a body. SPAD circuit 508-1 is configured to output a predetermined amount of current when SPAD 506-1 detects a photon. The predetermined amount of current is output throughout a duration of a predetermined measurement time period. Each of the outputs of SPAD circuits 508-1, 508-2, through 508-N are accumulated to provide an accumulated output at an output 510 of photodetector array 502. As each SPAD detects a photon, its corresponding SPAD circuit outputs the predetermined amount of current, contributing to the accumulated output. Thus, by sampling the accumulated output, the photodetector system (e.g., a processor of the photodetector system) may determine a temporal distribution of the photons detected. In configuration 500, the accumulated output is sampled by an ADC 512. ADC 512 may be implemented in any suitable manner, examples of which are described herein.

Figure 6:
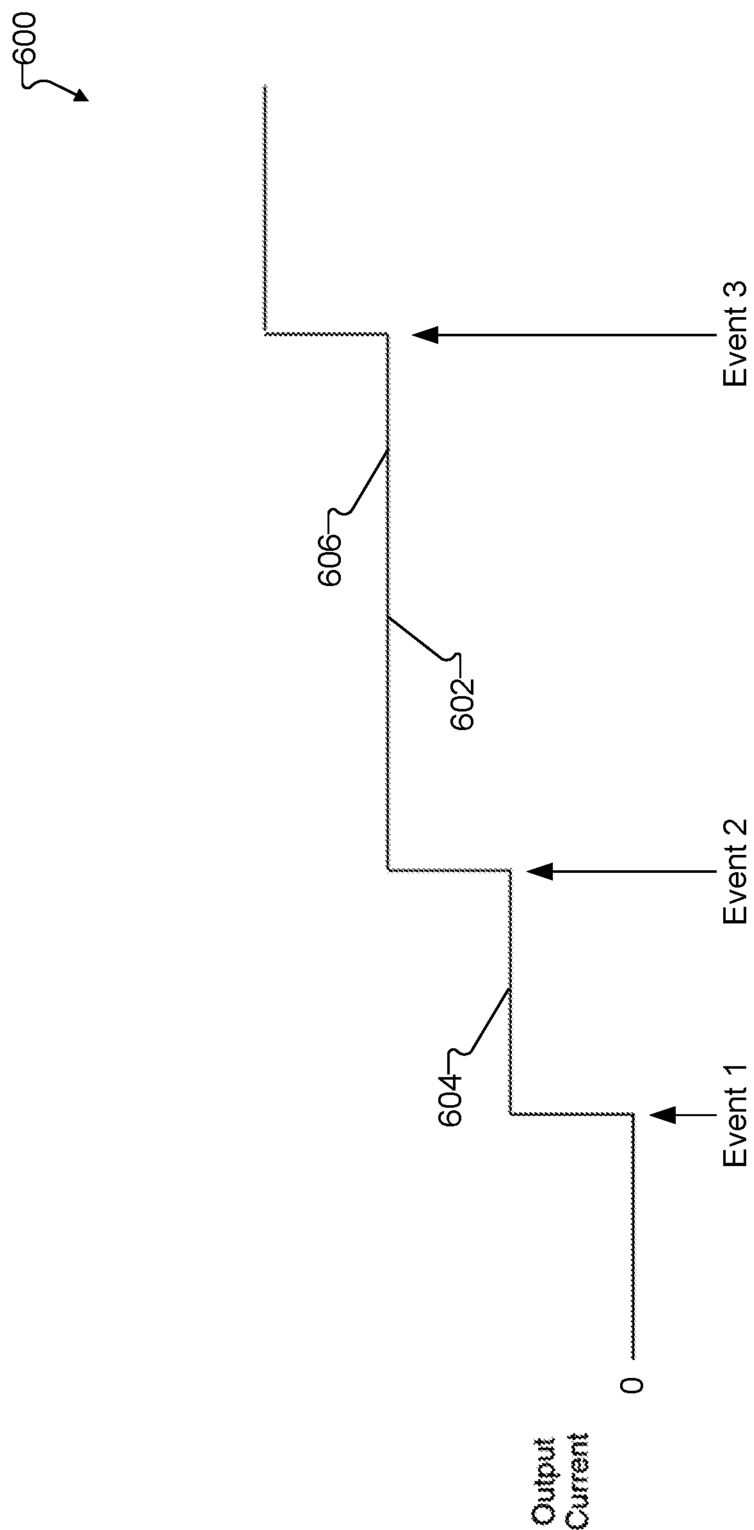
FIG. 6 illustrates an exemplary output diagram for TCSPC using photodetector architectures according to principles described herein.

For example, FIG. 6 shows an exemplary output diagram 600 for TCPSC with an analog implementation of a photodetector system (e.g., using photodetector array 502). Output diagram 600 shows an example accumulated output 602 of photodetector array 502 for a single laser pulse. Accumulated output 602 starts at zero until a first photon is detected at event 1 by, for instance, photodetector 504-1. Corresponding SPAD circuit 508-1 outputs the predetermined amount of current, raising accumulated output 602 from zero to a first current level 604, which is equal to the predetermined amount of current. At event 2, a second photon is detected, for instance, by photodetector 504-2. SPAD circuit 508-2 accordingly outputs the predetermined amount of current starting at event 2, thus raising accumulated output 602 from first current level 604 to second current level 606, which is equal to twice the predetermined amount of current. This is because both SPAD circuit 508-1 and SPAD circuit 508-2 are outputting the predetermined amount of current to output 510. Each additional detected photon raises accumulated output 602 by the predetermined amount of current, which is shown a final time at event 3. By sampling accumulated output 602, current levels of accumulated output 602 and times corresponding to changes in the current levels (and consequently, times for each of events 1, 2, 3, etc.) may be identified to determine the temporal distribution of detected photons.

Accumulated output 602 may be sampled in any suitable manner. For example, a sampling circuit may include a suitably fast analog-to-digital converter (ADC) (e.g., an ADC with a 10-30 gigabit per second (Gbps) sampling rate) that may be used to capture the temporal distribution. With such an ADC, the ADC may have a least significant bit (LSB) that is a small fraction of an average per photodetector current. The ADC may also have a dynamic range that is larger than a total current contributed by a whole activated photodetector array (e.g., a number of photodetectors in the photodetector array multiplied by the predetermined amount of current). The sampling circuit may also include a terminating component configured to convert the accumulated output to an output voltage. For instance, the terminating component may be implemented by a transimpedance amplifier (TIA) configured to buffer the accumulated output. Additionally or alternatively, the terminating component may be implemented by a termination resistor. The output voltage produced by the terminating component may be proportional to a total number of photodetectors that detected photons in the predetermined measurement time period.

Figure 7:
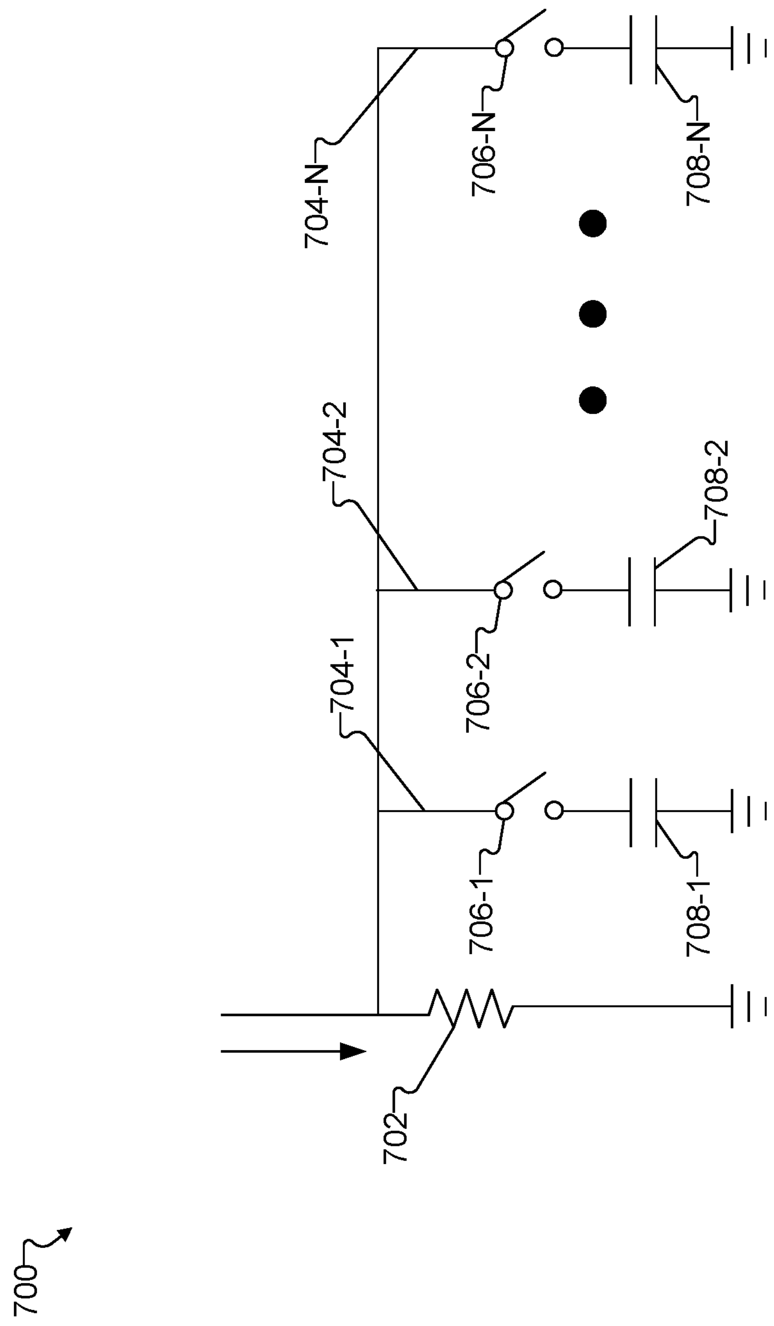
FIG. 7 illustrates an exemplary sampling circuit of a photodetector system for TCSPC according to principles described herein.

FIG. 7 illustrates another exemplary sampling circuit 700 of a photodetector system for sampling an accumulated output (e.g., accumulated output 602) of a photodetector array for TCSPC. Sampling circuit 700 includes a termination resistor 702 as a terminating component to convert the accumulated output to an output voltage. Sampling circuit 700 also includes a plurality of sampling branches 704 (sampling branches 704-1 through 704-N) connected in parallel to termination resistor 702. Sampling branches 704 each include a sampling switch 706 (sampling switches 706-1 through 706-N) and a sampling capacitor 708. For example, sampling branch 704-1 includes a sampling switch 706-1 and a sampling capacitor 708-1.

Sampling switches 706 are configured to be opened successively with a desired timing resolution (e.g., a switch every 50 ps, 20 ps, 100 ps, or any suitable timing resolution). As each sampling switch 706 is opened, corresponding sampling capacitor 708 will hold the output voltage at a respective sampling time of the timing resolution. For instance, if sampling switches 706 are opened every 50 ps, sampling switch 706-1 may be opened at 50 ps, with sampling capacitor 708-1 holding a first sampled output voltage at 50 ps, sampling switch 706-2 may be opened at 100 ps, with sampling capacitor 708-2 holding a second sampled output voltage at 100 ps, etc. through N sampling times. Holding the sampled output voltages with sampling capacitors 708 may allow sampling circuit 700 to include a relatively slow ADC to read out each of the sampled voltages.

The timing of sampling switches 706 may be controlled in any suitable manner. As an example, the timing may be controlled by a delay-locked loop (DLL) to generate precisely aligned phases that are separated by the timing resolution. Additionally or alternatively, more than one timing resolution may be used. For instance, referring back to histogram 300, a majority of the photons may be detected within a portion of the predetermined measurement time period. In histogram 300, the portion is between time bins 2.5 and 4. Sampling circuit 700 may be configured to sample a portion of interest (e.g., between times 2.5 and 4) at a higher sampling rate than a remainder of the predetermined measurement time period. Using a plurality of timing resolutions may allow for more efficient allocation of resources, using fewer sampling branches for the remainder of the predetermined measurement time period and using more sampling branches for the portion or portions of interest.

Figure 8:
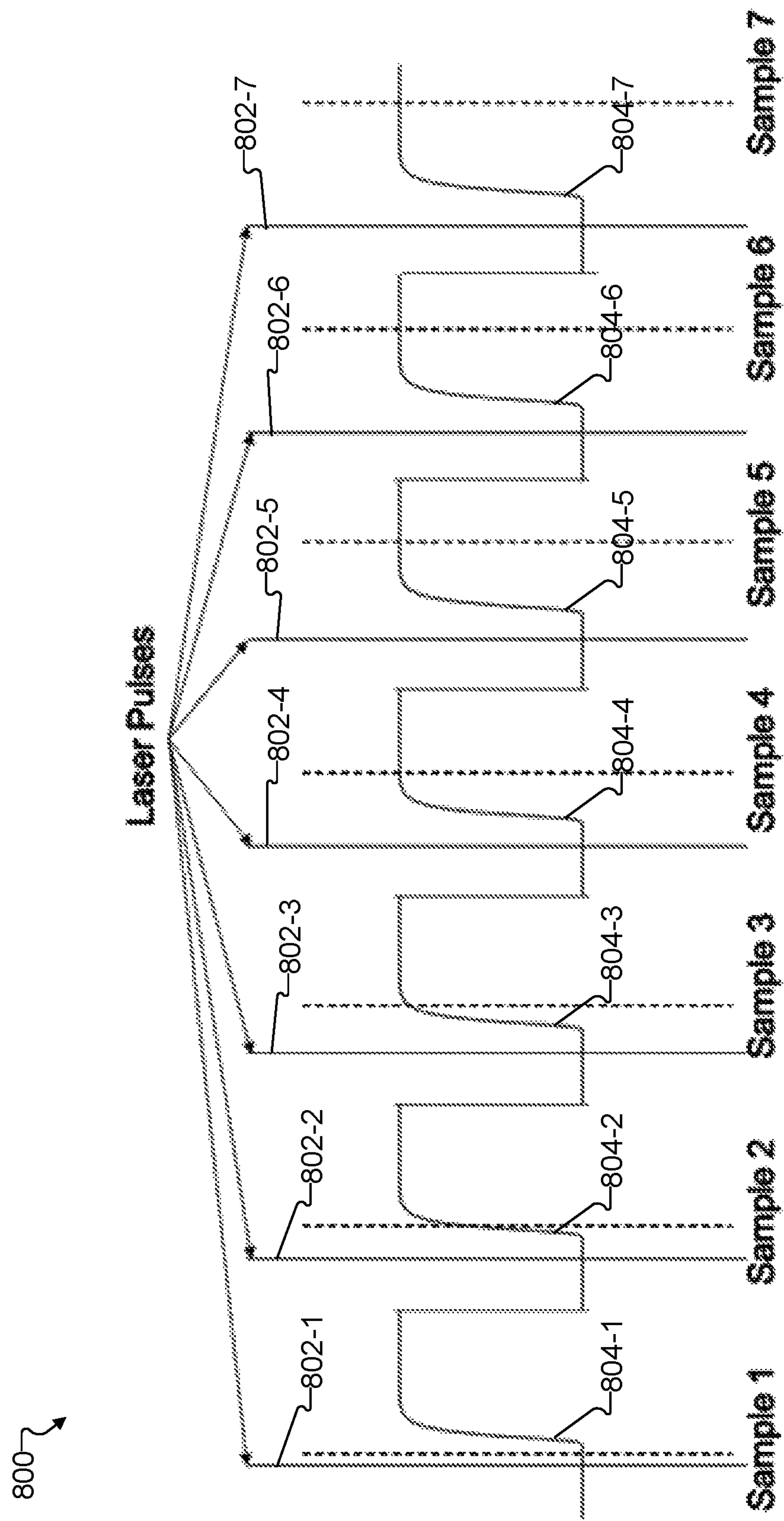
FIG. 8 illustrates an exemplary sampling timing diagram for TCSPC using photodetector architectures according to principles described herein.

FIG. 8 illustrates an exemplary sampling timing diagram 800 for sampling an accumulated output of a photodetector array for TCSPC that may be used in accordance with the systems and methods described herein. Sampling timing diagram 800 shows a plurality of laser pulses 802 (laser pulses 802-1 through 802-7). Each laser pulse 802 is followed by an accumulated output 804 (accumulated outputs 804-1 through 804-7) to be sampled. An ADC may be used to sample accumulated outputs 804 at a sampling rate equal to a rate of the laser pulses plus a particular delay time. As shown, sample 1 is taken of accumulated output 804-1 at a particular time (e.g., 1 ns) after laser pulse 802-1. Sample 2 is taken of accumulated output 804-2 at 2 ns after laser pulse 802-2. Sample 3 is taken of accumulated output 804-3 at 3 ns after laser pulse 802-3. In this manner, a slow ADC may be used to acquire samples of different time bins of different response outputs, rather than trying to sample all the time bins of each response output. However, as laser pulses 802 are repeated and accumulated outputs 804 are also repeated responses used to statistically generate a histogram, sampling different response outputs may provide a substantially similar histogram as sampling each response output.

Figure 9:
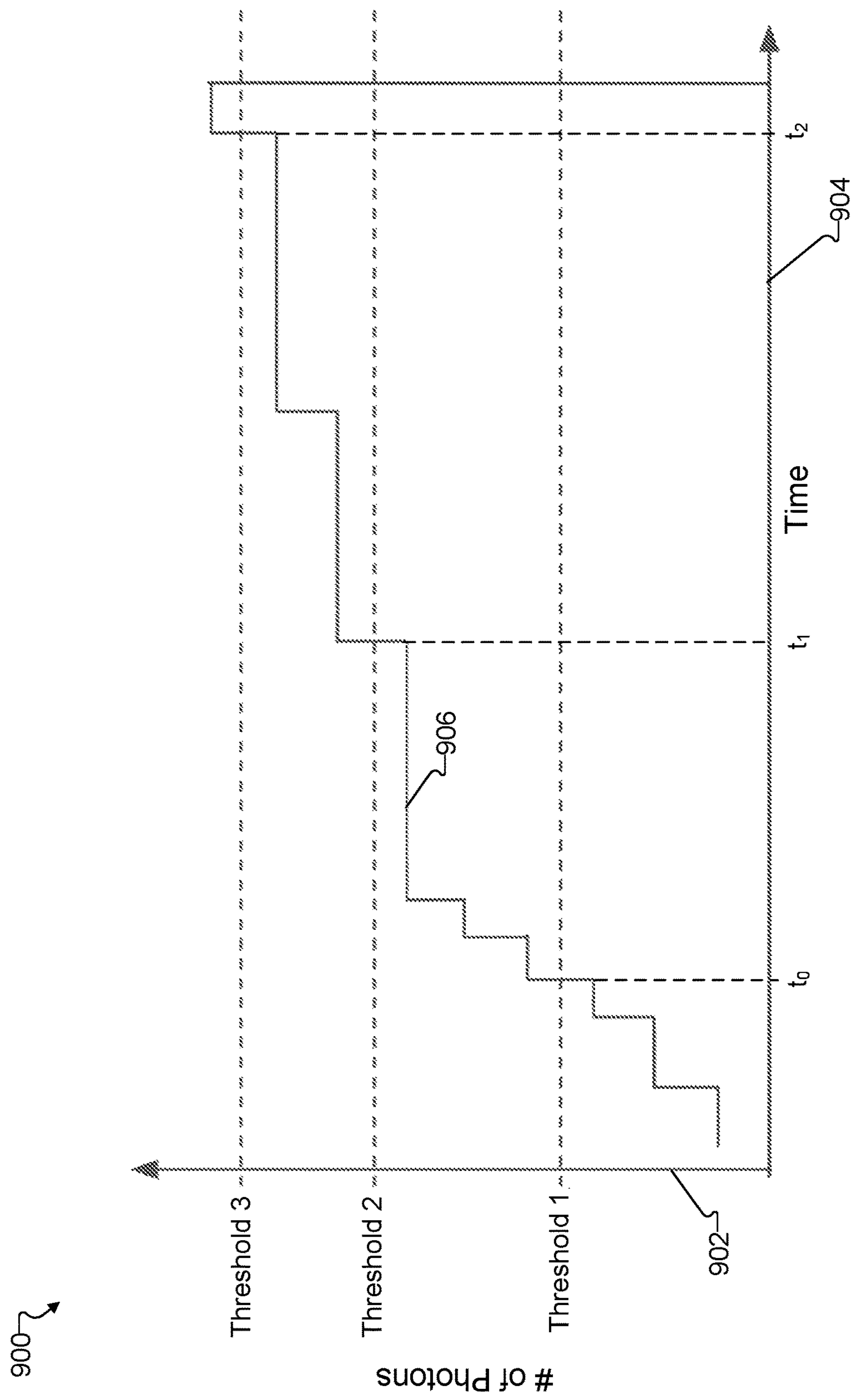
FIG. 9 illustrates an exemplary sampling diagram for TCSPC using photodetector architectures according to principles described herein.

FIG. 9 illustrates another exemplary sampling diagram 900 for sampling an accumulated output of a photodetector array for TCSPC that may be used in accordance with the systems and methods described herein. Sampling diagram 900 shows a number of photons on a y-axis 902 and a time on an x-axis 904. Sampling diagram 900 shows thresholds of interest for numbers of photons at Threshold 1, Threshold 2, and Threshold 3. Sampling diagram 900 also shows an accumulated output 906. An ADC may be used to sample accumulated output 906, focusing on thresholds of interest. At each point that accumulated output 906 meets a threshold of interest, a time is determined for the meeting of the threshold. In this example, Threshold 1 is met at time $t_0$, Threshold 2 is met at time $t_1$, and Threshold 3 is met at time $t_2$. Focusing on such thresholds may allow for more efficient allocation of resources.

Figure 10:
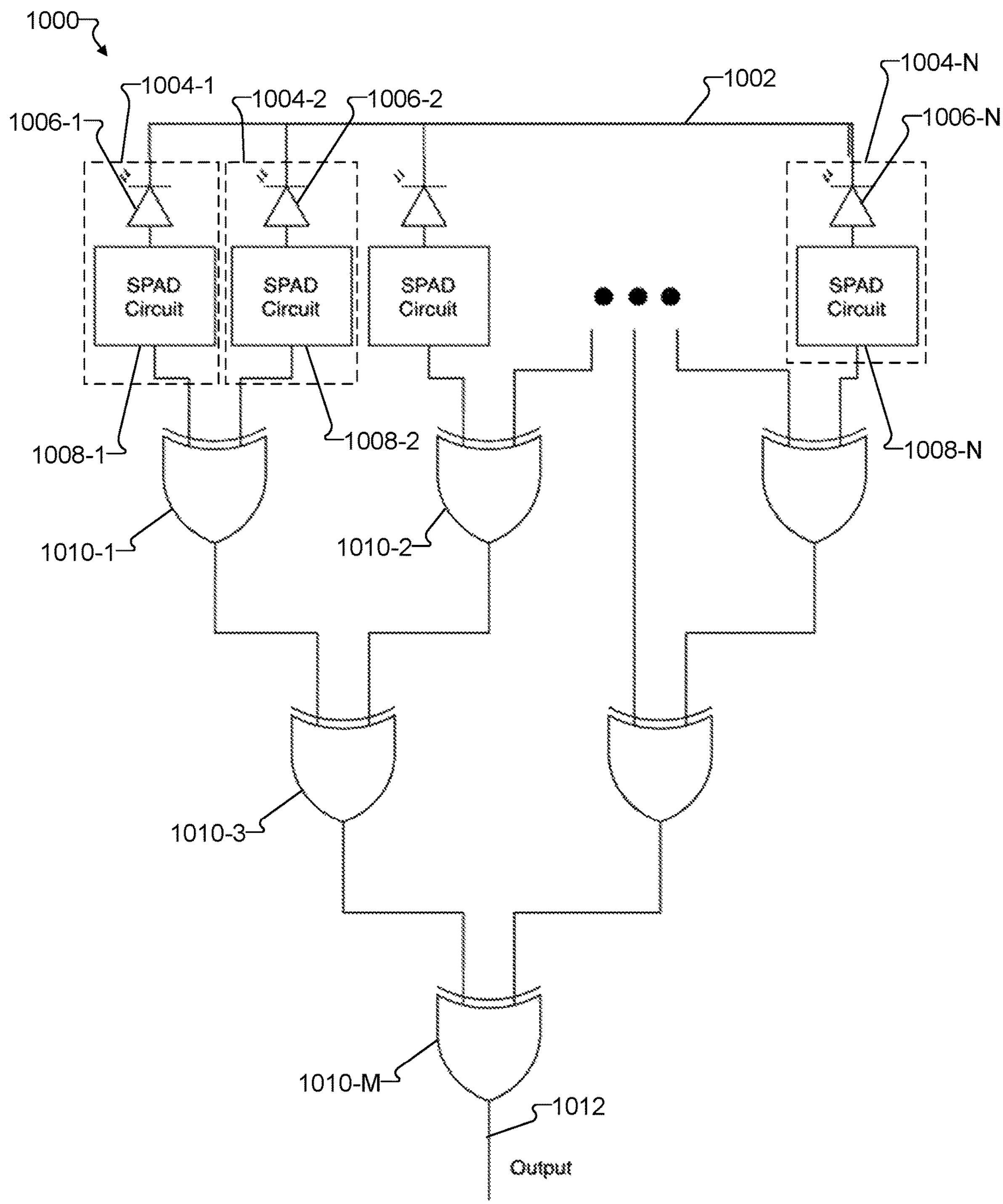
FIG. 10 illustrates an exemplary photodetector array of a photodetector system for TCSPC according to principles described herein.

FIG. 10 illustrates an exemplary configuration 1000 of a photodetector array 1002 (e.g., an implementation of photodetector array 104) that may be part of an exemplary digital implementation of a photodetector system for TCSPC. Photodetector array 1002 includes a plurality of photodetectors 1004 (photodetectors 1004-1 through 1004-N) connected in parallel. In configuration 1000, photodetectors 1004 each include a SPAD 1006 (SPAD 1006-1 through 1006-N) and a SPAD circuit 1008 (SPAD circuit 1008-1 through 1008-N). For example, photodetector 1004-1 includes a SPAD 1006-1 and a SPAD circuit 1008-1.

In the digital implementation, SPAD circuits 1008 are each configured to output a high state of a digital signal when corresponding SPAD 1006 detects a photon. For example, if SPAD 1006-1 detects a photon, SPAD circuit 1008-1 outputs a high signal (e.g., a high state of a digital signal). As in the analog implementation, the photodetector system may abstain from resetting SPADs 1006 during a predetermined measurement time period. Thus, outputs of SPAD circuits 1008 may be held high upon detection of a photon by a corresponding SPAD 1006. In this manner, the outputs of SPAD circuits 1008 are accumulated to provide an accumulated output at an output 1012 of photodetector array 1002.

The outputs of each SPAD circuit 1008 may be accumulated in any suitable manner. As an example, the outputs may be accumulated using a tree of XOR gates 1010 (an XOR tree). In this example, each SPAD circuit 1008 may feed into an XOR gate. As shown, SPAD circuits 1008-1 and 1008-2 feed into an XOR gate 1010-1. The next two SPAD circuits feed into a next XOR gate 1010-2. XOR gates 1010-1 and 1010-2 in turn feed into another XOR gate 1010-3, such that each SPAD circuit 1008 feeds into an XOR gate 1010 with an adjacent SPAD circuit and each XOR gate 1010, along with an adjacent XOR gate, feeds into another XOR gate downstream until the outputs are accumulated into an accumulated output at output 1012.

When any SPAD 1006 detects a photon and corresponding SPAD circuit 1008 outputs a high signal, the XOR gate 1010 receiving the high signal will also output a high signal. The high signals will propagate down a corresponding branch of the XOR tree, changing the accumulated output from low to high. If another photon is detected by another SPAD 1006, the XOR gate receiving the high signal will flip, whether from high to low or low to high. This signal will also propagate down a corresponding branch of the XOR tree until the accumulated output is flipped from high to low. Thus, with each photon detected by photodetector array 1002, the accumulated output will toggle between logic states (e.g., from low to high and from high to low). By sampling the accumulated output to count toggles and determine times of the toggles, the photodetector system may determine a temporal distribution of detected photons. Based on the temporal distribution of photons, the photodetector system may generate a histogram representing a light pulse response of a target.

Figure 11:
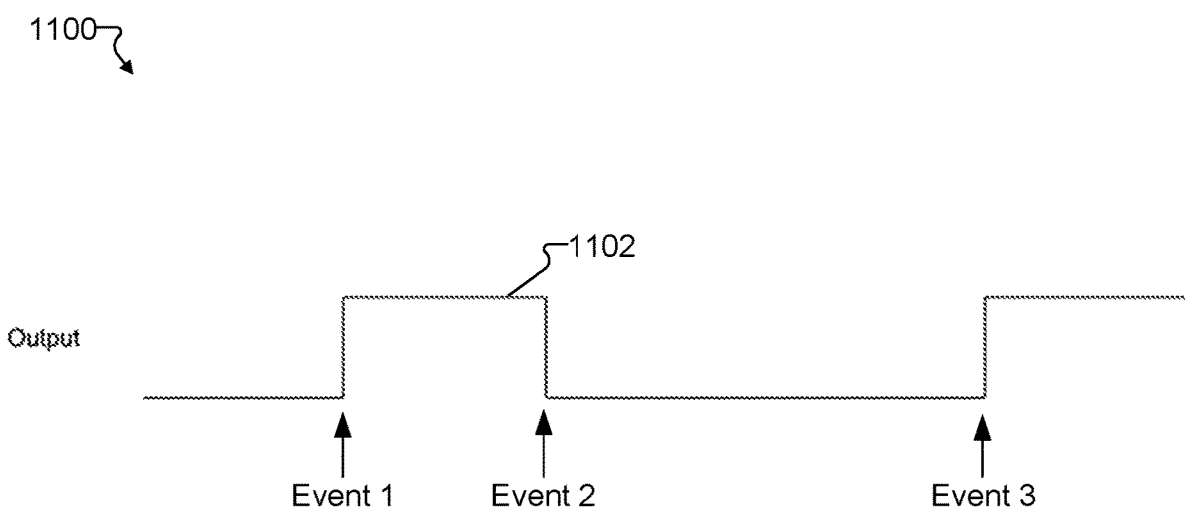
FIG. 11 illustrates an exemplary output diagram of a photodetector system for TCSPC according to principles described herein.

For example, FIG. 11 shows an exemplary output diagram 1100 for TCPSC with a digital implementation of a photodetector system (e.g., using photodetector array 1002). Output diagram 1100 shows an example accumulated output 1102 of photodetector array 1002 for a single laser pulse. Accumulated output 1102 starts low until a first photon is detected at event 1. The first photon may be detected, for instance, by photodetector 1004-1. In response, corresponding SPAD circuit 1008-1 outputs a high signal, changing an output of XOR gate 1010-1 from low to high, which in turn does the same for XOR gates 1010-3 and 1010-M, toggling accumulated output 1102 from low to high. At event 2, a second photon is detected, for instance, by photodetector 1004-2. In response, SPAD circuit 1008-2 also outputs a high signal, toggling the output of XOR gate 1010-1 back from high to low, which in turn does the same for XOR gates 1010-3 and 1010-M, toggling accumulated output 1102 from high to low. Each additional detected photon toggles accumulated output 1102 from one logic state to the other, which is shown a final time at event 3. By sampling accumulated output 1102, logic states of accumulated output 1102 and times corresponding to changes in the logic states (and consequently, times for each of events 1, 2, 3, etc.) may be identified to determine the temporal distribution of detected photons.

Accumulated output 1102 may be sampled in any suitable manner. For example, a sampling circuit may include a time-to-digital converter (TDC) configured to detect changes in logic states of accumulated output 1102 and identify times of the changes.

In some examples of the digital implementation, if two photons are detected by SPADs sufficiently close together in time (e.g., within a threshold amount of time), a collision event may occur. With some collision events, accumulated output 1102 may toggle twice very quickly and both changes in logic states may be missed by the TDC. With other collision events, accumulated output 1102 may not toggle at all, or toggle fewer times than photons detected by SPADs. Hence, in some examples, the photodetector system may include a collision detection circuit configured to detect such collision events to minimize potential errors in counting photons.

The collision detection circuit may be implemented in any suitable manner. For example, the collision detection circuit may include an OR tree routed alongside the XOR tree shown in FIG. 10. The OR tree may include an additional circuit at an input of the OR tree to generate a pulse. If an output of the OR tree goes high for a pulse (e.g., 50-200 ps) while the output of the XOR tree does not change, then that would indicate a collision event.

Additionally or alternatively, the collision detection circuit may include one or more components configured to determine how many of the photodetectors in the photodetector array have detected photons during the predetermined measurement time period. By determining a sum of SPADs that have fired during the predetermined measurement time period and comparing the sum to a total number of toggles detected, a number of collision events may be determined by calculating a difference between the sum of fired SPADs and the total number of toggles.

Figure 12:
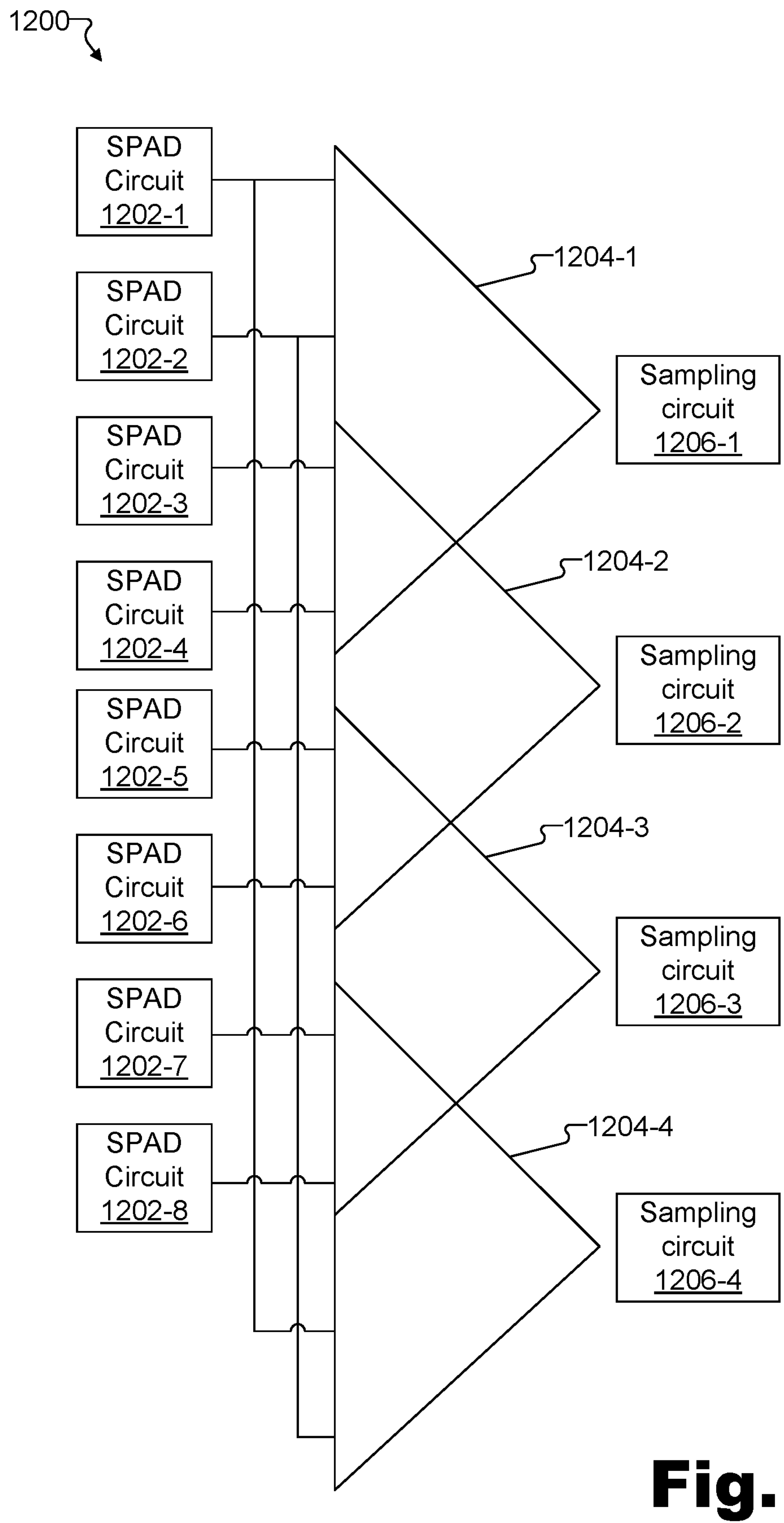
FIG. 12 illustrates an exemplary collision detection circuit of a photodetector system for TCPSC according to principles described herein.

Additionally or alternatively, FIG. 12 illustrates another exemplary collision detection circuit 1200 of a photodetector system for TCPSC that may be used in accordance with the systems and methods described herein. Collision detection circuit 1200 shows a plurality of SPAD circuits 1202 (SPAD circuits 1202-1 through 1202-8). Each SPAD circuit 1202 feeds into more than one XOR tree 1204 (XOR trees 1204-1 through 1204-4). In this example, SPAD circuits 1202-1 and 1202-2 feed into XOR trees 1204-1 and 1204-4, SPAD circuits 1202-3 and 1202-4 feed into XOR trees 1204-1 and 1204-2, etc. Each XOR tree 1204 is sampled by a separate sampling circuit 1206 (sampling circuits 1206-1 through 1206-4). By outputting each SPAD circuit 1202 into more than one XOR tree 1204, a probability of collision events is reduced, as even if one pair of SPADs detects photons within a threshold amount of time, each SPAD of the pair may be detected correctly in another sampling circuit 1206.

Figure 13:
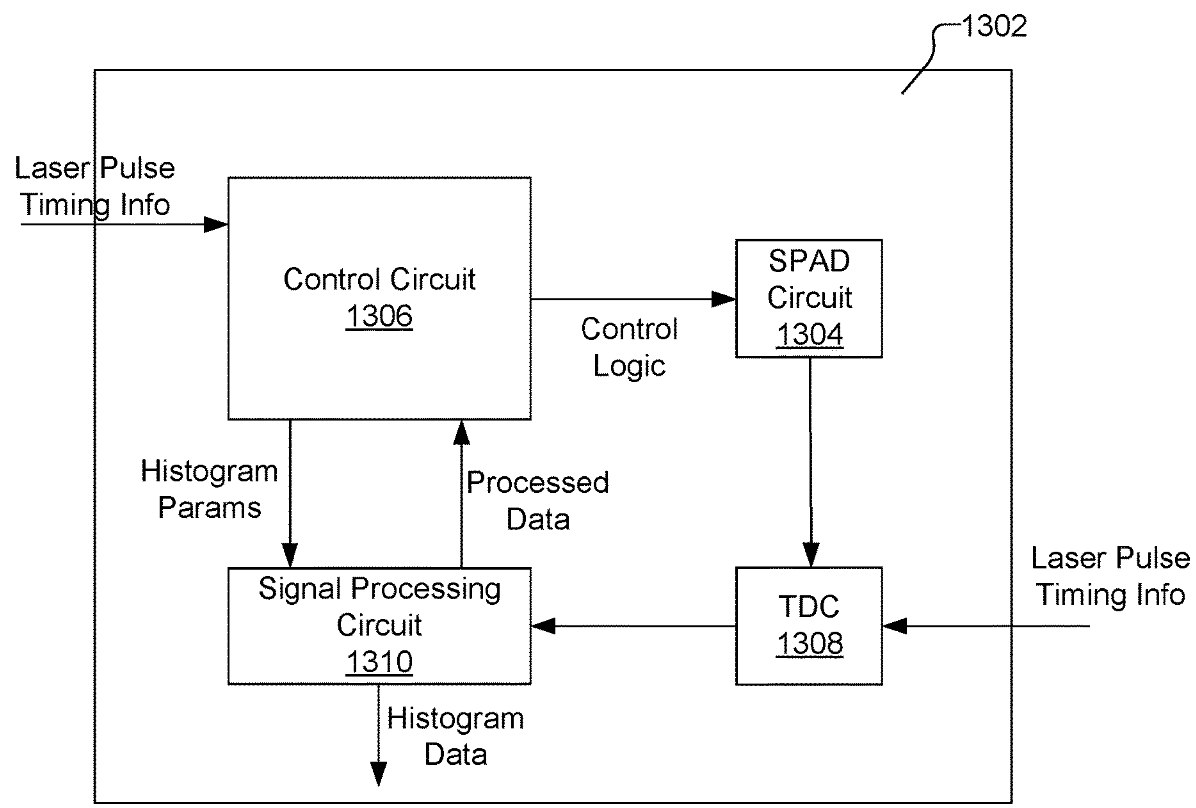
FIG. 13 illustrates an exemplary photodetector of a photodetector system for TCPSC according to principles described herein.

FIG. 13 illustrates various components included in an exemplary photodetector 1302 that may be used in accordance with the systems and methods described herein. Photodetector 1302 may implement, for example, any of photodetectors 106 shown in FIG. 1 and/or any of the other photodetectors described herein. As shown, photodetector 1302 includes a SPAD circuit 1304, a control circuit 1306, a TDC 1308, and a signal processing circuit 1310.

SPAD circuit 1304 may include a SPAD and a fast gating circuit configured to operate together to detect a photon incident upon the SPAD. As described above, SPAD circuit 1304 may generate an output when SPAD circuit 1304 detects a photon.

Control circuit 1306 may be implemented by an application specific integrated circuit (ASIC) or any other suitable circuit configured to control an operation of various components within SPAD circuit 1304. For example, control circuit 1306 may output control logic that controls an operation of one or more switches within SPAD circuit 1304 to selectively charge a capacitor within SPAD circuit 1304 and put the SPAD included in the SPAD circuit 1304 in either an armed or a disarmed state. In some examples, control circuit 1306 may control a gate delay, which specifies a predetermined amount of time control circuit 1306 is to wait after an occurrence of a light pulse (e.g., a laser pulse) to put the SPAD in the armed state. To this end, control circuit 1306 may receive light pulse timing information, which indicates a time at which a light pulse occurs (e.g., a time at which the light pulse is applied to tissue within the brain). Control circuit 1306 may also control a programmable gate width, which specifies how long the SPAD is kept in the armed state before being disarmed.

Control circuit 1306 is further configured to control signal processing circuit 1310. For example, control circuit 1306 may provide histogram parameters (e.g., time bins, number of light pulses, type of histogram, etc.) to signal processing circuit 1310. Signal processing circuit 1310 may generate histogram data in accordance with the histogram parameters.

TDC 1308 is configured to measure a time difference between an occurrence of an output pulse generated by SPAD circuit 1304 and an occurrence of a light pulse. To this end, TDC 1308 may also receive the same light pulse timing information that control circuit 1306 receives. TDC 1308 may be implemented by any suitable circuitry as may serve a particular implementation.

Signal processing circuit 1310 is configured to perform one or more signal processing operations on data output by TDC 1308. For example, signal processing circuit 1310 may generate histogram data based on the data output by TDC 1308 and in accordance with histogram parameters provided by control circuit 1306. To illustrate, signal processing circuit 1310 may generate, store, transmit, compress, analyze, decode, and/or otherwise process histograms based on the data output by TDC 1308. In some examples, signal processing circuit 1310 may provide processed data to control circuit 1306, which may use the processed data in any suitable manner.

Figure 14A:
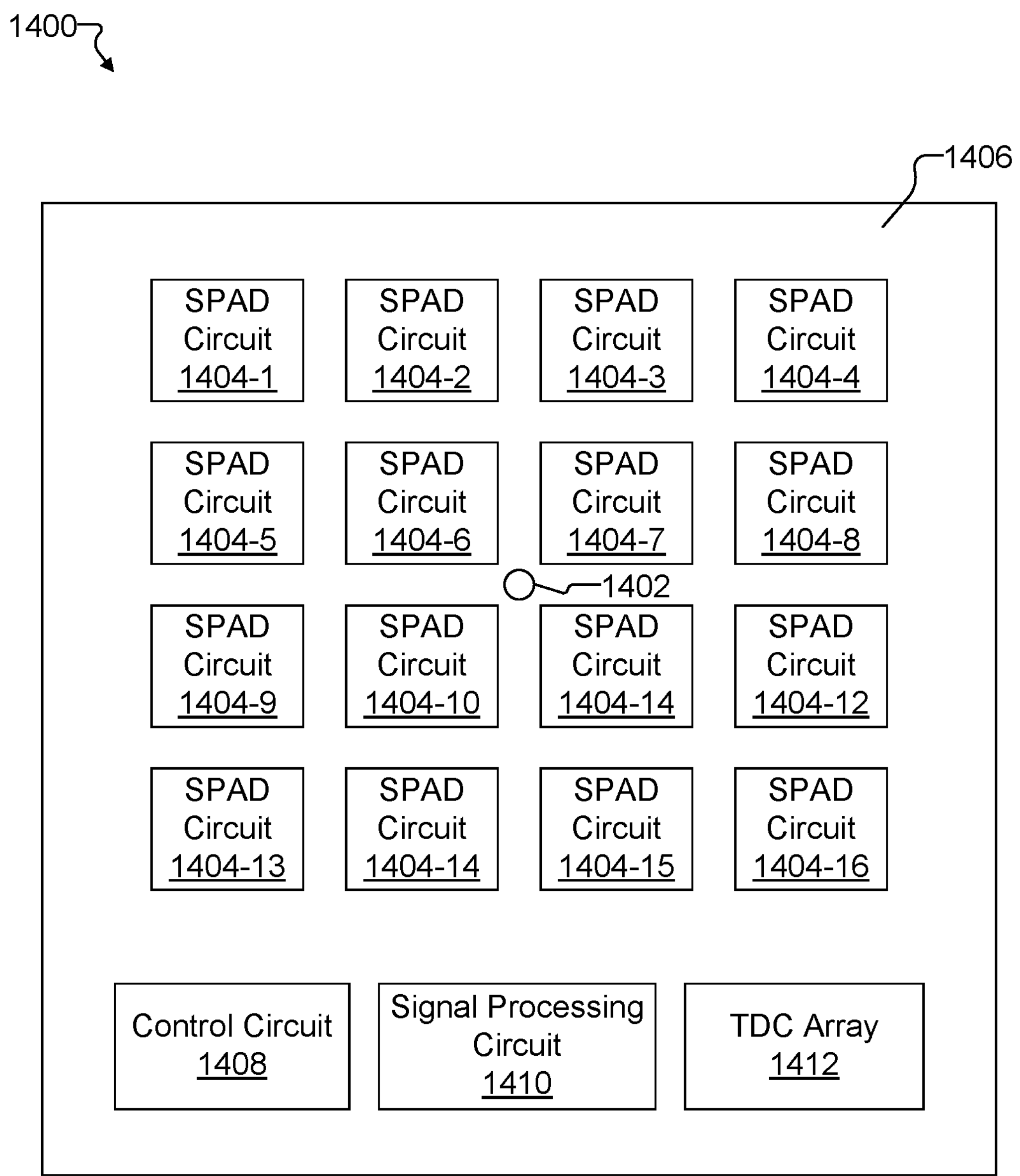
FIG. 14A illustrates an exemplary photodetector system for TCPSC according to principles described herein.

FIG. 14A illustrates an exemplary photodetector system 1400 that may be used in accordance with the systems and methods described herein. Photodetector system 1400 may implement any of the photodetector systems described herein. As shown, photodetector system 1400 includes a light source 1402 and a plurality of SPAD circuits 1404 (i.e., SPAD circuits 1404-1 through 1404-16) disposed on a printed circuit board (PCB) 1406. Alternatively, SPAD circuits 1404 (and the other components of photodetector system 1400) may be disposed on an ASIC. Photodetector system 1400 further includes a control circuit 1408 common to SPADs 1404, a signal processing circuit 1410 common to SPADs 1404, and a TDC array 1412 that includes a plurality of TDCs each corresponding to one of the SPAD circuits 1404. Control circuit 1408, signal processing circuit 1410, and TDC array 1412 may each be disposed on PCB 1406, as shown in FIG. 14A, or located elsewhere within photodetector system 1400. Each SPAD circuit 1404 in combination with a TDC included in TDC array 1412, control circuit 1408, and signal processing circuit 1404 may implement a particular photodetector. Hence, photodetector system 1400 may be said to include an array of photodetectors.

Light source 1402 may be configured to generate one or more light pulses at one or more wavelengths that may be applied to a desired target (e.g., a target within the brain). Light source 1402 may be implemented by any suitable combination of components. For example, light source 1402 may be implemented by a laser source that generates laser pulses. Light source may be implemented on PCB 1406 or external to PCB 1406.

SPAD circuits 1404 are each similar in operation to SPAD circuit 1304 and may be configured to detect photons of a light pulse generated by light source 1402 after the photons reflect or scatter from a target (e.g., a target internal to a user, such as brain tissue). SPAD circuits 1404 may also be used to detect photons reflected from any object due to ambient light for imaging applications. In this case, light source 1402 is not needed since the photons are generated by either ambient light or another light source.

As shown, SPAD circuits 1404 are arranged in a four-by-four array on PCB 1406. The positioning of each SPAD circuit 1404 may correspond, for example, to a pixel within a pixel array. SPAD circuits 1404 may alternatively be arranged in any suitable manner. While sixteen SPAD circuits 1404 are shown in FIG. 14A, it will be recognized that any number of SPAD circuits 1404 may be included in photodetector system 1400.

Control circuit 1408 may be similar in function to control circuit 1306, and may be configured to control each of SPAD circuits 1408. Signal processing circuit 1410 may be similar in function to signal processing circuit 1310, and may be configured to process signals output by each of SPAD circuits 1404. TDC array 1412 may include a plurality of TDCs each similar to TDC 1308 and configured to measure a time difference between the occurrence of a light pulse 1402 and output pulses generated by each of SPAD circuits 1404.

Photodetector system 1400 may be implemented by or included in any suitable device. For example, photodetector system 1400 may be included in a non-invasive wearable device that a user may wear to perform one or more diagnostic, imaging, and/or consumer-related operations.

Figure 14B:
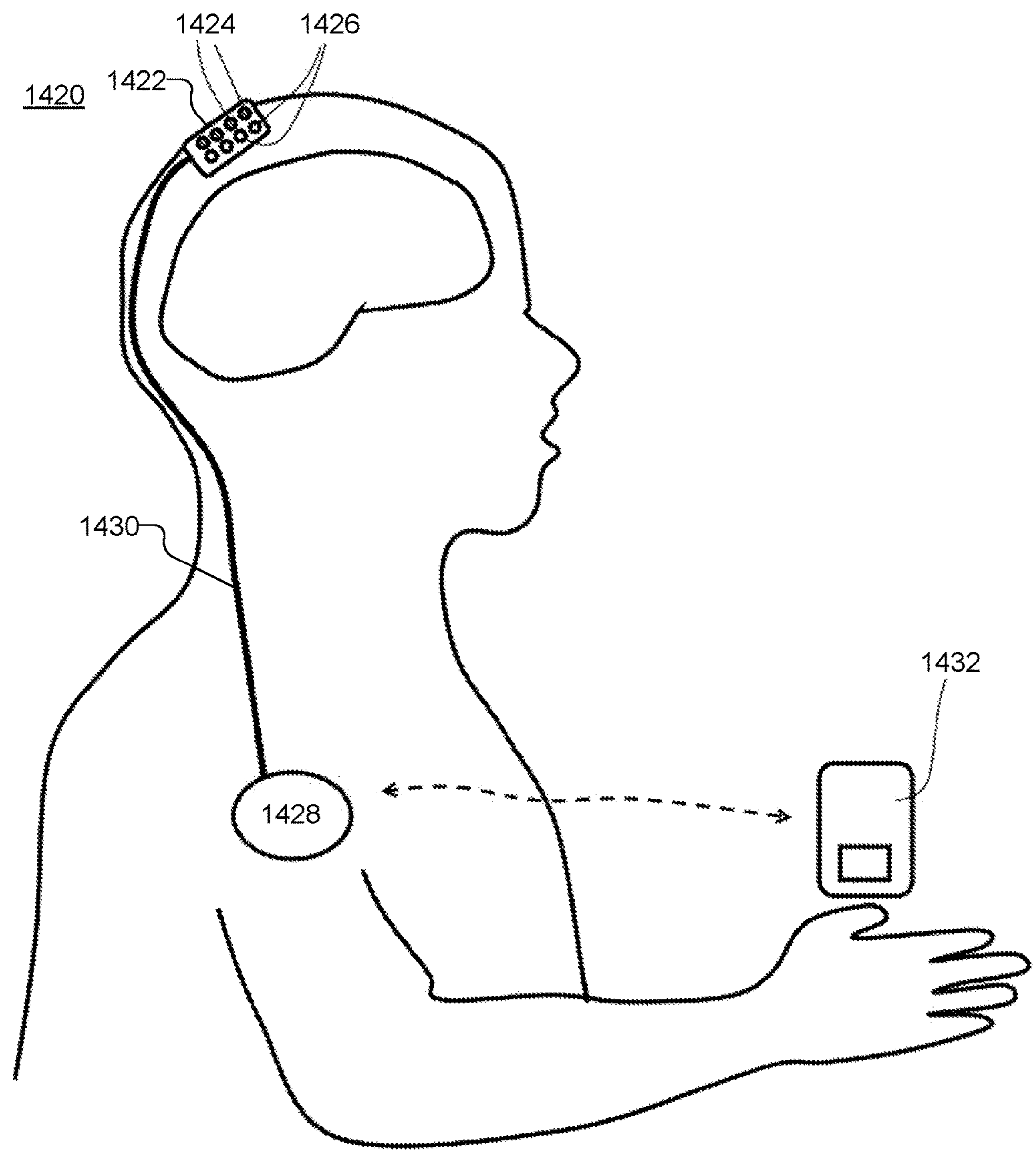
FIG. 14B illustrates an exemplary wearable device including a photodetector system for TCSPC according to principles described herein.

To illustrate, FIG. 14B shows an exemplary non-invasive wearable brain interface system 1420 ("brain interface system 1420") that implements a photodetector system, which may be similar to photodetector system 1400. As shown, brain interface system 1420 includes a head-mountable component 1422 configured to be attached to a user's head. Head-mountable component 1422 may be implemented by a cap shape that is worn on a head of a user. Alternative implementations of head-mountable component 1422 include helmets, beanies, headbands, other hat shapes, or other forms conformable to be worn on a user's head, etc. Head-mountable component 1422 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 1422 includes a plurality of photodetectors 1424 and a plurality of light sources 1426 configured to generate light pulses. It will be recognized that in some alternative embodiments, head-mountable component 1422 may include a single photodetector 1424 and/or a single light source 1426. For example, brain interface system 1420 may be used for controlling an optical path and for transforming photodetector pixel measurements into an intensity value that represents an optical property of a brain tissue region. Brain interface system 1420 allows optical detection of deep anatomical location through skin and bone by extracting data from photons originating from light source 1426 to a target location within the user's brain, in contrast to traditional imaging systems and methods (e.g., optical coherence tomography (OCT)), which only image superficial tissue structures or through optically transparent structures.

Brain interface system 1420 may further include a processor 1428 configured to communicate with (e.g., control and/or receive signals from) photodetectors 1424 and light sources 1426 by way of a communication link 1430. Communication link 1430 may include any suitable wired and/or wireless communication link. Processor 1428 may include any suitable housing and may be located on the user's scalp, neck, shoulders, chest, or arm, as may be desirable. In some variations, processor 1428 may be integrated in the same assembly housing as photodetectors 1424 and light sources 1426.

As shown, brain interface system 1420 may optionally include a remote processor 1432 in communication with processor 1428. For example, remote processor 1432 may store measured data from photodetectors 1424 and/or processor 1428 from previous detection sessions and/or from multiple brain interface systems (not shown). Power for photodetectors 1424, light sources 1426, and/or processor 1428 may be provided via a wearable battery (not shown). In some examples, processor 1428 and the battery may be enclosed in a single housing, and wires carrying power signals from processor 1428 and the battery may extend to photodetectors 1424 and light sources 1426. Alternatively, power may be provided wirelessly (e.g., by induction).

In some alternative embodiments, head mountable component 1422 does not include individual light sources. Instead, a light source configured to generate the light that is detected by photodetector 1424 may be included elsewhere in brain interface system 1420. For example, a light source may be included in processor 1428 and coupled to photodetector units 1424 through electrical connections.

Each of the light sources described herein may be implemented by any suitable device. For example, a light source as used herein may be, for example, a distributed feedback (DFB) laser, a super luminescent diode (SLD), a light emitting diode (LED), a diode-pumped solid-state (DPSS) laser, a laser diode (LD), a super luminescent light emitting diode (sLED), a vertical-cavity surface-emitting laser (VCSEL), a titanium sapphire laser, a micro light emitting diode (mLED), and/or any other suitable laser or light source.

Photodetector system 1400 shown in FIG. 14A may alternatively be included in a non-wearable device (e.g., a medical device and/or consumer device that is placed near the head or other body part of a user to perform one or more diagnostic, imaging, and/or consumer-related operations). Photodetector system 1400 may alternatively be included in a sub-assembly enclosure of a wearable invasive device (e.g., an implantable medical device for brain recording and imaging).

Any suitable SPAD circuits may be used in the photodetector architectures described herein. Some of the SPAD circuits described herein are gated with a capacitor (or, in some cases, with a parasitic capacitance of the SPAD itself) that is pre-charged with a bias voltage before a command is provided to arm the SPAD. This is described more fully in U.S. Pat. No. 10,158,038, incorporated above by reference in its entirety.

Figure 15:
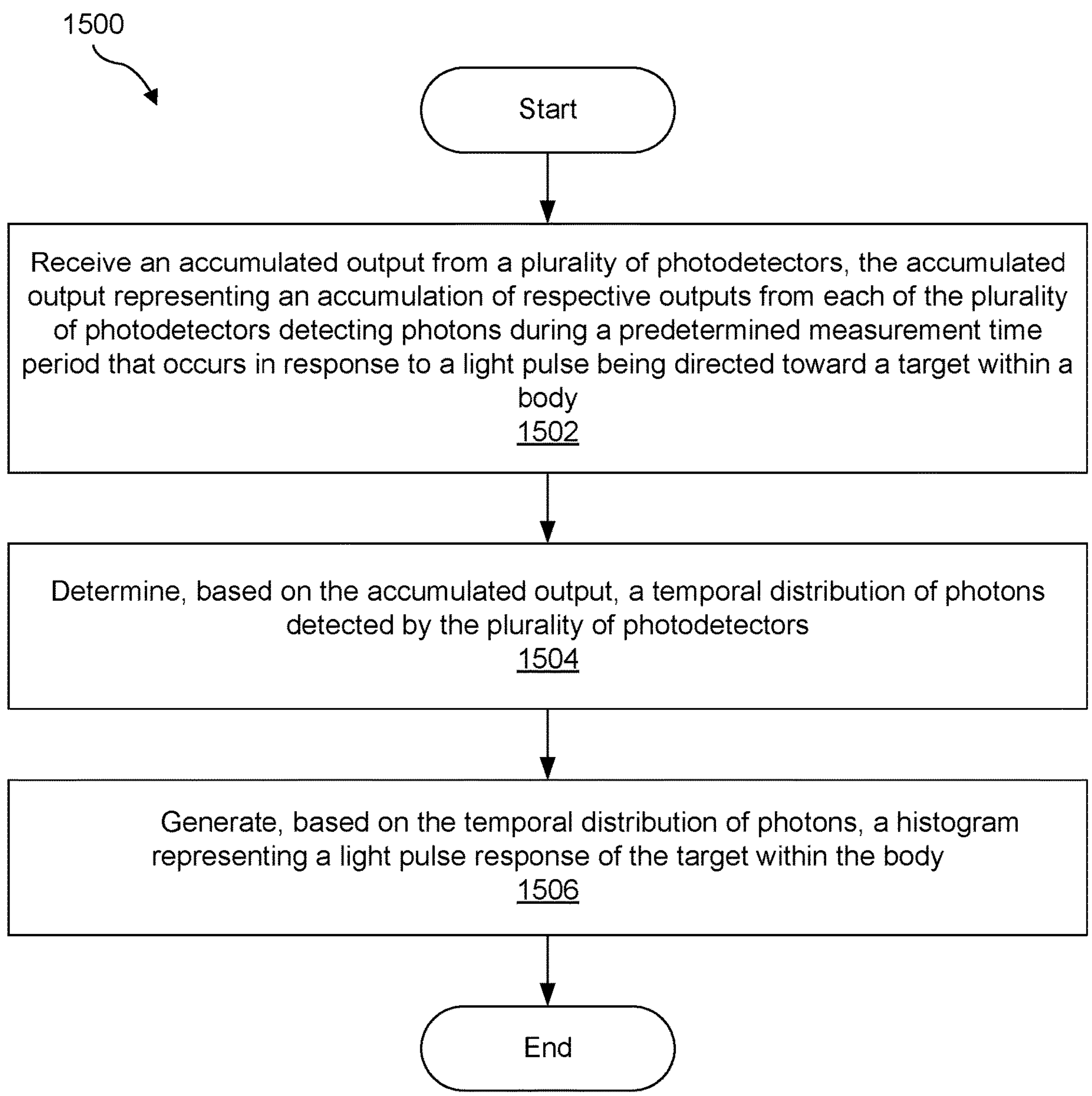
FIG. 15 illustrates an exemplary method according to principles described herein.

FIG. 15 illustrates an exemplary method 1500 for performing TCSPC using a photodetector system (e.g., any of the photodetector systems described herein). While FIG. 15 illustrates exemplary operations according to one embodiment, other embodiments may omit, add to, reorder, and/or modify any of the operations shown in FIG. 15.

In operation 1502, a processor receives an accumulated output from a plurality of photodetectors, the accumulated output representing an accumulation of respective outputs from each of the plurality of photodetectors detecting photons during a predetermined measurement time period that occurs in response to a light pulse being directed toward a target within a body. Operation 1502 may be performed in any of the ways described herein.

In operation 1504, the processor determines, based on the accumulated output, a temporal distribution of photons detected by the plurality of photodetectors. Operation 1504 may be performed in any of the ways described herein.

In operation 1506, the processor generates, based on the temporal distribution of photons, a histogram representing a light pulse response of the target within the body. Operation 1506 may be performed in any of the ways described herein.

Figure 16:
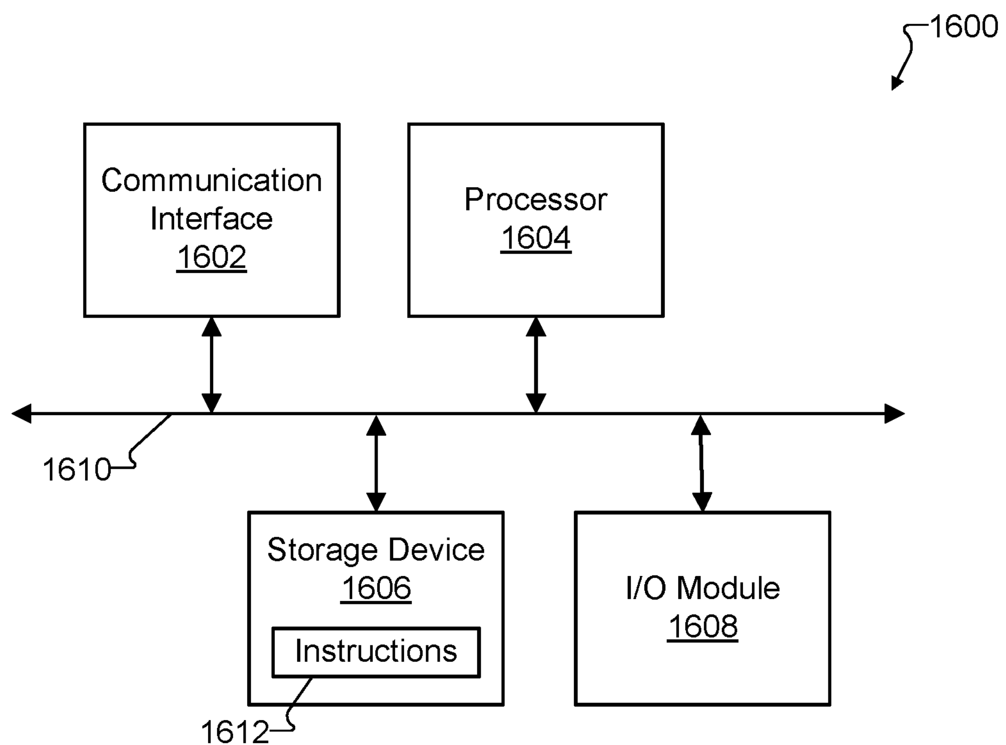
FIG. 16 illustrates an exemplary computing device according to principles described herein.

FIG. 16 illustrates an exemplary computing device 1600 that may be specifically configured to perform one or more of the processes described herein. As shown in FIG. 16, computing device 1600 may include a communication interface 1602, a processor 1604, a storage device 1606, and an input/output ("I/O") module 1608 communicatively connected one to another via a communication infrastructure 1610. While an exemplary computing device 1600 is shown in FIG. 16, the components illustrated in FIG. 16 are not intended to be limiting. Additional or alternative components may be used in other embodiments. Components of computing device 1600 shown in FIG. 16 will now be described in additional detail.

Communication interface 1602 may be configured to communicate with one or more computing devices. Examples of communication interface 1602 include, without limitation, a wired network interface (such as a network interface card), a wireless network interface (such as a wireless network interface card), a modem, an audio/video connection, and any other suitable interface.

Processor 1604 generally represents any type or form of processing unit capable of processing data and/or interpreting, executing, and/or directing execution of one or more of the instructions, processes, and/or operations described herein. Processor 1604 may perform operations by executing computer-executable instructions 1612 (e.g., an application, software, code, and/or other executable data instance) stored in storage device 1606.

Storage device 1606 may include one or more data storage media, devices, or configurations and may employ any type, form, and combination of data storage media and/or device. For example, storage device 1606 may include, but is not limited to, any combination of the non-volatile media and/or volatile media described herein. Electronic data, including data described herein, may be temporarily and/or permanently stored in storage device 1606. For example, data representative of computer-executable instructions 1612 configured to direct processor 1604 to perform any of the operations described herein may be stored within storage device 1606. In some examples, data may be arranged in one or more databases residing within storage device 1606.

I/O module 1608 may include one or more I/O modules configured to receive user input and provide user output. I/O module 1608 may include any hardware, firmware, software, or combination thereof supportive of input and output capabilities. For example, I/O module 1608 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1608 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1608 is configured to provide graphical data to a display for presentation to a user. The graphical data may be representative of one or more graphical user interfaces and/or any other graphical content as may serve a particular implementation.

In some examples, any of the systems, computing devices, processors, controller units, and/or other components described herein may be implemented by computing device 1600. For example, processor 108 and/or controller unit 112 may be implemented by processor 1604.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:

a plurality of photodetectors connected in parallel, respective outputs from each of the plurality of photodetectors each comprising a predetermined amount of current output when a respective photodetector included in the plurality of photodetectors detects a photon of a light pulse after the light pulse reflects from a target within a body;

an analog-to-digital converter (ADC) coupled to the plurality of photodetectors;

a terminating component configured to convert a combined current of an accumulated output from the plurality of photodetectors to an output voltage;

a plurality of sampling branches connected in parallel with the terminating component, each sampling branch of the plurality of sampling branches comprising a switch and a capacitor; and a processor communicatively coupled to the plurality of photodetectors and the ADC, the processor configured to:

receive the accumulated output from the plurality of photodetectors, the accumulated output representing an accumulation of the respective outputs from each of the plurality of photodetectors detecting photons during a predetermined measurement time period that occurs in response to the light pulse being directed toward the target within the body;

determine, based on the accumulated output, a temporal distribution of photons detected by the plurality of photodetectors by directing the ADC to sample the output voltage; and generate, based on the temporal distribution of photons, a histogram representing a light pulse response of the target within the body.

2. The system of claim 1, wherein the processor is further configured to:

reset the plurality of photodetectors subsequent to the predetermined measurement time period;

receive an additional accumulated output from the plurality of photodetectors, the additional accumulated output representing an additional accumulation of respective outputs from each of the plurality of photodetectors detecting photons during an additional predetermined measurement time period that occurs in response to an additional light pulse being directed toward the target within the body; and determine, based on the additional accumulated output, an additional temporal distribution of photons detected by the plurality of photodetectors, wherein the generating the histogram is further based on the additional temporal distribution of photons.

3. The system of claim 2, wherein the histogram represents a cumulative distribution of photons detected for a plurality of predetermined measurement time periods including the predetermined measurement time period and the additional predetermined measurement time period, the plurality of predetermined measurement time periods each occurring in response to respective light pulses of a plurality of light pulses being directed toward the target within the body, the plurality of light pulses including the light pulse and the additional light pulse, and wherein the processor is further configured to:

generate, based on the cumulative distribution, a temporal point spread function further representing the light pulse response of the target within the body.

4. The system of claim 1, wherein the processor is further configured to abstain from resetting the plurality of photodetectors during the predetermined measurement time period.

5. The system of claim 1, wherein the directing the ADC to sample the output voltage comprises directing the ADC to sample the output voltage at a first sampling rate for a first portion of the predetermined measurement time period and at a second sampling rate for a second portion of the predetermined measurement time period.

6. The system of claim 1, wherein:

the light pulse is one of a plurality of light pulses directed toward the target within the body, the plurality of light pulses applied at a particular rate; and the sampling the accumulated output comprises sampling the output voltage at a sampling rate that is slower than the particular rate of the plurality of light pulses.

7. The system of claim 6, wherein the sampling rate is based on a combination of the particular rate of the plurality of light pulses and a particular delay time.

8. The system of claim 1, wherein each photodetector of the plurality of photodetectors comprises:

a single photon avalanche diode (SPAD); and a fast gating circuit configured to arm and disarm the SPAD.

9. The system of claim 8, further comprising a non-invasive wearable device housing the plurality of photodetectors.

10. The system of claim 9, further comprising a light source configured to generate the light pulse, the light source housed in the non-invasive wearable device.

11. The system of claim 9, wherein the non-invasive wearable device is configured to be worn on a head of a user, and wherein the target within the body comprises an area in a brain of the user.

12. The system of claim 11, wherein the processor is further configured to determine, based on the histogram, a neural activity in the brain of the user.

13. The system of claim 1, wherein the switches of the plurality of sampling branches are configured to open successively at a sampling rate, and wherein the directing the ADC to sample the output voltage comprises directing the ADC to access voltage measurements of the capacitor of each of the sampling branches.

14. A system comprising:

a plurality of photodetectors, each photodetector of the plurality of photodetectors comprising:

a single photon avalanche diode (SPAD), and a fast gating circuit configured to arm and disarm the SPAD, each photodetector configured to provide an output comprising a predetermined amount of current when the photodetector detects a photon of a light pulse during a predetermined measurement time period after the light pulse reflects from a target within a body, the plurality of photodetectors connected in parallel to provide an accumulated current combining the respective outputs from each photodetector of the plurality of photodetectors;

an analog-to-digital converter (ADC) coupled to the plurality of photodetectors;

a terminating component configured to convert the accumulated current to an output voltage;

a plurality of sampling branches connected in parallel with the terminating component, each sampling branch of the plurality of sampling branches comprising a switch and a capacitor; and a processor communicatively coupled to the plurality of photodetectors and the ADC, the processor configured to:

direct the ADC to sample the output voltage;

determine, based on the sampled output voltage, a temporal distribution of photons detected by the plurality of photodetectors; and generate, based on the temporal distribution of photons, a histogram representing a light pulse response of the target within the body.

15. The system of claim 14, wherein the processor is further configured to:

reset the plurality of photodetectors subsequent to the predetermined measurement time period;

receive an additional accumulated output from the plurality of photodetectors, the additional accumulated output representing an additional accumulation of respective outputs from each of the plurality of photodetectors detecting photons during an additional predetermined measurement time period that occurs in response to an additional light pulse being directed toward the target within the body; and determine, based on the additional accumulated output, an additional temporal distribution of photons detected by the plurality of photodetectors, wherein the generating the histogram is further based on the additional temporal distribution of photons.

16. The system of claim 15, wherein:

the histogram represents a cumulative distribution of photons detected for a plurality of predetermined measurement time periods including the predetermined measurement time period and the additional predetermined measurement time period, the plurality of predetermined measurement time periods each occurring in response to respective light pulses of a plurality of light pulses being directed toward the target within the body, the plurality of light pulses including the light pulse and the additional light pulse, and the processor is further configured to generate, based on the cumulative distribution, a temporal point spread function further representing the light pulse response of the target within the body.

17. The system of claim 14, wherein the processor is further configured to abstain from resetting the plurality of photodetectors during the predetermined measurement time period.

18. The system of claim 14, wherein the directing the ADC to sample the output voltage comprises directing the ADC to sample the output voltage at a first sampling rate for a first portion of the predetermined measurement time period and at a second sampling rate for a second portion of the predetermined measurement time period.

19. The system of claim 14, wherein:

the light pulse is one of a plurality of light pulses directed toward the target within the body, the plurality of light pulses applied at a particular rate; and the sampling the accumulated output comprises sampling the output voltage at a sampling rate that is slower than the particular rate of the plurality of light pulses.

20. The system of claim 19, wherein the sampling rate is based on a combination of the particular rate of the plurality of light pulses and a particular delay time.

21. The system of claim 14, further comprising a non-invasive wearable device housing the plurality of photodetectors.

22. The system of claim 21, further comprising a light source configured to generate the light pulse, the light source housed in the non-invasive wearable device.

23. The system of claim 21, wherein the non-invasive wearable device is configured to be worn on a head of a user, and wherein the target within the body comprises an area in a brain of the user.

24. The system of claim 23, wherein the processor is further configured to determine, based on the histogram, a neural activity in the brain of the user.

25. The system of claim 14, wherein the switches of the plurality of sampling branches are configured to open successively at a sampling rate, and wherein the directing the ADC to sample the output voltage comprises directing the ADC to access voltage measurements of the capacitor of each of the sampling branches.

26. A system comprising:

a plurality of photodetectors, each photodetector of the plurality of photodetectors configured to provide an output comprising a digital signal indicating whether a respective photodetector included in the plurality of photodetectors has detected a photon of a light pulse during a predetermined measurement time period after the light pulse reflects from a target within a body;

an XOR tree comprising a plurality of XOR gates combining the respective outputs of each photodetector of the plurality of photodetectors to provide a combined signal configured to toggle based on the respective outputs;

a time-to-digital converter (TDC) coupled to the plurality of photodetectors;

a collision detection circuit coupled to the plurality of photodetectors, the collision detecting circuit comprising an OR tree comprising a plurality of OR gates combining the respective outputs from each of the plurality of photodetectors; and a processor communicatively coupled to the plurality of photodetectors, the collision detection circuit, and the TDC, the processor configured to:

direct the TDC to sample the combined signal;

direct the collision detection circuit to detect a collision event where a first photon is detected by a first photodetector of the plurality of photodetectors and a second photon is detected, within a threshold amount of time, by a second photodetector of the plurality of photodetectors;

determine, based on the sampled combined signal and an output of the collision detection circuit, a temporal distribution of photons detected by the plurality of photodetectors; and generate, based on the temporal distribution of photons, a histogram representing a light pulse response of the target within the body.

27. The system of claim 26, wherein the processor is further configured to:

reset the plurality of photodetectors subsequent to the predetermined measurement time period;

receive an additional combined signal from the plurality of photodetectors, the additional combined signal representing an additional accumulation of respective outputs from each of the plurality of photodetectors detecting photons during an additional predetermined measurement time period that occurs in response to an additional light pulse being directed toward the target within the body; and determine, based on the additional combined signal, an additional temporal distribution of photons detected by the plurality of photodetectors, wherein the generating the histogram is further based on the additional temporal distribution of photons.

28. The system of claim 27, wherein the histogram represents a cumulative distribution of photons detected for a plurality of predetermined measurement time periods including the predetermined measurement time period and the additional predetermined measurement time period, the plurality of predetermined measurement time periods each occurring in response to respective light pulses of a plurality of light pulses being directed toward the target within the body, the plurality of light pulses including the light pulse and the additional light pulse, and wherein the processor is further configured to:

generate, based on the cumulative distribution, a temporal point spread function further representing the light pulse response of the target within the body.

29. The system of claim 26, wherein the processor is further configured to abstain from resetting the plurality of photodetectors during the predetermined measurement time period.

30. The system of claim 26, wherein the collision detection circuit is configured to determine how many of the plurality of photodetectors have detected photons during the predetermined measurement time period, and wherein the directing the collision detection circuit to detect the collision event comprises comparing a number of toggles of the combined signal during the predetermined measurement time period to a number of the plurality of photodetectors that have detected photons during the predetermined measurement time period.

31. The system of claim 26, wherein the XOR tree is one of a plurality of XOR trees, wherein the respective outputs from each of the plurality of photodetectors is combined in at least two of the plurality of XOR trees, and wherein the directing the collision detection circuit to detect the collision event comprises comparing outputs from the plurality of XOR trees.

32. The system of claim 26, further comprising a non-invasive wearable device housing the plurality of photodetectors.

33. The system of claim 32, further comprising a light source configured to generate the light pulse, the light source housed in the non-invasive wearable device.

34. The system of claim 32, wherein the non-invasive wearable device is configured to be worn on a head of a user, and wherein the target within the body comprises an area in a brain of the user.

35. The system of claim 34, wherein the processor is further configured to determine, based on the histogram, a neural activity in the brain of the user.

36. The system of claim 26, wherein the directing the collision detection circuit to detect the collision event comprises detecting a change in an output of the OR tree that does not correspond to a change in the combined signal.

37. The system of claim 26, wherein each photodetector of the plurality of photodetectors comprises:

a single photon avalanche diode (SPAD); and a fast gating circuit configured to arm and disarm the SPAD.

38. A method comprising:

receiving, by a processor, an accumulated output from a plurality of photodetectors connected in parallel, the accumulated output representing an accumulation of respective outputs from each of the plurality of photodetectors detecting photons during a predetermined measurement time period that occurs in response to a light pulse being directed toward a target within a body;

determining, by the processor and based on the accumulated output, a temporal distribution of photons detected by the plurality of photodetectors by directing an analog-to-digital converter (ADC) coupled to the plurality of photodetectors, the processor, and a plurality of sampling branches connected in parallel with a terminating component, each sampling branch of the plurality of sampling branches comprising a switch and a capacitor, the processor directing the ADC to access voltage measurements of the capacitor of each of the sampling branches; and generating, by the processor and based on the temporal distribution of photons, a histogram representing a light pulse response of the target within the body, wherein the respective outputs from each of the plurality of photodetectors each comprise a predetermined amount of current output when a respective photodetector included in the plurality of photodetectors detects a photon of the light pulse after the light pulse reflects from the target, the accumulated output comprises a combined current based on a combination of the respective outputs, and the terminating component is configured convert the combined current to an output voltage.

39. The method of claim 38, further comprising:

resetting, by the processor, the plurality of photodetectors subsequent to the predetermined measurement time period;

receiving, by the processor, an additional accumulated output from the plurality of photodetectors, the additional accumulated output representing an additional accumulation of respective outputs from each of the plurality of photodetectors detecting photons during an additional predetermined measurement time period that occurs in response to an additional light pulse being directed toward the target within the body; and determining, by the processor and based on the additional accumulated output, an additional temporal distribution of photons detected by the plurality of photodetectors, wherein the generating the histogram is further based on the additional temporal distribution of photons.

40. The method of claim 39, wherein the histogram represents a cumulative distribution of photons detected for a plurality of predetermined measurement time periods including the predetermined measurement time period and the additional predetermined measurement time period, the plurality of predetermined measurement time periods each occurring in response to respective light pulses of a plurality of light pulses being directed toward the target within the body, the plurality of light pulses including the light pulse and the additional light pulse, and wherein the method further comprises generating, by the processor, based on the cumulative distribution, a temporal point spread function further representing the light pulse response of the target within the body.

41. The method of claim 38, further comprising abstaining, by the processor, from resetting the plurality of photodetectors during the predetermined measurement time period.

42. The method of claim 38, wherein the directing the ADC comprises directing the ADC to sample the output voltage at a first sampling rate for a first portion of the predetermined measurement time period and at a second sampling rate for a second portion of the predetermined measurement time period.

43. The method of claim 38, wherein:

the light pulse is one of a plurality of light pulses directed toward the target within the body, the plurality of light pulses applied at a particular rate; and the directing the ADC comprises directing the ADC to sample the output voltage at a sampling rate that is slower than the particular rate of the plurality of light pulses.

44. The method of claim 43, wherein the sampling rate is based on a combination of the particular rate of the plurality of light pulses and a particular delay time.

45. The method of claim 38, further comprising determining, by the processor, based on the histogram, a neural activity in a brain of a user.

46. The method of claim 38, further comprising directing, by the processor, the plurality of sampling branches to each switch successively at a sampling rate.

47. A method comprising:

receiving, by a processor, an accumulated output from a plurality of photodetectors connected in parallel, the accumulated output representing an accumulation of respective outputs from each of the plurality of photodetectors detecting photons during a predetermined measurement time period that occurs in response to a light pulse being directed toward a target within a body, wherein:

each of the respective outputs from the plurality of photodetectors is configured to provide a digital signal indicating whether a respective photodetector included in the plurality of photodetectors has detected a photon, the respective outputs are combined using an XOR tree comprising a plurality of XOR gates, and the accumulated output comprises a combined signal configured to toggle between logic states based on the respective outputs;

directing, by the processor, a collision detection circuit coupled to the plurality of photodetectors and the processor to detect a collision event where a first photon is detected by a first photodetector of the plurality of photodetectors and a second photon is detected, within a threshold amount of time, by a second photodetector of the plurality of photodetectors, the collision detection circuit comprising an OR tree comprising a plurality of OR gates combining the respective outputs from each of the plurality of photodetectors;

determining, by the processor and based on the accumulated output and an output of the collision detection circuit, a temporal distribution of photons detected by the plurality of photodetectors by directing a time-to-digital converter (TDC) coupled to the plurality of photodetectors and the processor to sample the combined signal; and generating, by the processor and based on the temporal distribution of photons, a histogram representing a light pulse response of the target within the body.

48. The method of claim 47, wherein the directing the collision detection circuit to detect the collision event comprises detecting a change in an output of the OR tree that does not correspond to a change in the accumulated output.

49. The method of claim 47, wherein the collision detection circuit is configured to determine how many of the plurality of photodetectors have detected photons during the predetermined measurement time period, and wherein the directing the collision detection circuit to detect the collision event comprises comparing a number of toggles of the accumulated output during the predetermined measurement time period to a number of the plurality of photodetectors that have detected photons during the predetermined measurement time period.

* * * * *